United States Patent
Contreras-Vidal et al.

(10) Patent No.: US 9,468,541 B2
(45) Date of Patent: Oct. 18, 2016

(54) TIME DOMAIN-BASED METHODS FOR NONINVASIVE BRAIN-MACHINE INTERFACES

(75) Inventors: Jose L. Contreras-Vidal, Houston, TX (US); Trent J. Bradberry, Arlington, VA (US); Rodolphe J. Gentili, Silver Spring, MD (US); Harshavardhan Agashe, Houston, TX (US)

(73) Assignee: University of Maryland College Park, College Park, MD (US)

( * ) Notice: Subject to any disclaimer, the term of this patent is extended or adjusted under 35 U.S.C. 154(b) by 408 days.

(21) Appl. No.: 13/695,631

(22) PCT Filed: May 5, 2011

(86) PCT No.: PCT/US2011/035299
§ 371 (c)(1),
(2), (4) Date: Apr. 26, 2013

(87) PCT Pub. No.: WO2011/140303
PCT Pub. Date: Nov. 10, 2011

(65) Prior Publication Data
US 2014/0058528 A1    Feb. 27, 2014

Related U.S. Application Data

(60) Provisional application No. 61/331,664, filed on May 5, 2010, provisional application No. 61/369,128, filed on Jul. 30, 2010.

(51) Int. Cl.
| | | |
|---|---|---|
| A61F 2/72 | (2006.01) | |
| A61B 5/0484 | (2006.01) | |
| A61B 5/0496 | (2006.01) | |
| A61B 5/0478 | (2006.01) | |
| A61B 5/04 | (2006.01) | |
| G06F 3/01 | (2006.01) | |

(52) U.S. Cl.
CPC ............ *A61F 2/72* (2013.01); *A61B 5/04012* (2013.01); *A61B 5/0478* (2013.01); *A61B 5/0496* (2013.01); *A61B 5/04842* (2013.01); *G06F 3/015* (2013.01); *A61B 5/04009* (2013.01); *G06F 3/013* (2013.01)

(58) Field of Classification Search
None
See application file for complete search history.

(56) References Cited

U.S. PATENT DOCUMENTS

| | | |
|---|---|---|
| 5,474,082 A | 12/1995 | Junker |
| 5,638,826 A | 6/1997 | Wolpaw et al. |
| 7,058,445 B2 | 6/2006 | Kemere et al. |
| 7,120,486 B2 | 10/2006 | Leuthardt et al. |

(Continued)

OTHER PUBLICATIONS

Nicolelis et al., Controlling Robots with the Mind, Scientific American, Oct. 2002, pp. 46-53.*

(Continued)

*Primary Examiner* — David H Willse
(74) *Attorney, Agent, or Firm* — AuerbachSchrot LLC; William C. Schrot

(57) ABSTRACT

A noninvasive brain computer interface (BCI) system includes an electroencephalography (EEG) electrode array configured to acquire EEG signals generated by a subject. The subject observes movement of a stimulus. A computer is coupled to the EEG electrode array and configured to collected and process the acquired EEG signals. A decoding algorithm is used that analyzes low-frequency (delta band) brain waves in the time domain to continuously decode neural activity associated with the observed movement.

12 Claims, 23 Drawing Sheets

(56) References Cited

U.S. PATENT DOCUMENTS

| | | | |
|---|---|---|---|
| 7,209,788 B2 | 4/2007 | Nicolelis et al. | |
| 7,299,089 B2 | 11/2007 | Wolf et al. | |
| 2003/0093129 A1* | 5/2003 | Nicolelis et al. | 607/45 |
| 2003/0100931 A1 | 5/2003 | Mullett | |
| 2004/0073414 A1 | 4/2004 | Bienenstock et al. | |
| 2005/0085744 A1 | 4/2005 | Beverina et al. | |
| 2006/0129277 A1 | 6/2006 | Wu et al. | |
| 2009/0221928 A1 | 9/2009 | Einav et al. | |
| 2010/0069780 A1 | 3/2010 | Schuette et al. | |
| 2010/0191140 A1* | 7/2010 | Terada et al. | 600/544 |

OTHER PUBLICATIONS

Acharya et al. (2010) "*Electrocorticographic amplitude predicts finger positions during slow grasping motions of the hand*," J. Neural Eng., 7(4):46002 (13 pages).
Boonstra et al. (2008) "*Gait disorders and balance disturbances in Parkinson's disease: clinical update and pathophysiology*," Cuur. Opin. Neurol., 21:461-471.
Bradberry et al (2008) "*Decoding hand and cursor kinematics from magnetoencephalographic signals during tool use*," Conf. Proc. Eng. Med. Biol. Soc. 2008:5306-5309.
Bradberry et al. (2009) "*Decoding center-out hand velocity from MEG signals during visuomotor adaptation*," Neuro-image, 47:1691-1700.
Bradberry et al. (2010) "*Reconstructing three-dimensional hand movements from noninvasive electrocephalographic signals*," J. Neurosci. 30:3432-3437.
Bradberry et al. (2011) "*Fast attainment of computer cursor control with noninvasively acquired brain signals*," J. Neural Engineering 8:036010 (9pp).
Carignan et al. (2008) "*Controlling shoulder impedance in a rehabilitation arm exoskeleton*," proc. IEEE Int. Conf. on Robotics and Automation (ICRA pp . 2453-2458.
Carmena et al. (2003) "*Learning to control a brain-machine interface for reaching and grasping by primates*," PLoS Biol., 1, E42:193-208.
Cisek et al. (2004) "*Neural correlates of mental rehearsal in dorsal premotor cortex*," Nature, 431:993-996.
Cohen et al. (2004) "*Reduction of single-neuron firing uncertainty by cortical ensembles during motor skill learning*," J. Neurosci., 24:3574-3582.
Delorme et al. (2004) "*EEGLAB: an open source toolbox for analysis of single-trial EEG dynamics including independent component analysis*," J. Neurosci. Methods, 134:9-21; http://sccn.ucsd.edu/eeglab.
Fitzsimmons et al. (2009) "*Extracting kinematic parameters for monkey walking from cortical neuronal ensemble activity*," Front. Integr. Neurosic., 3:3 doi: 10.3389/neuro.07.003.2009 pp. 1-19.
Frisoli et al. (2008) "*Robot mediated arm rehabilitation in virtual environments for chronic stroke patients: a clinical study*," Proc. IEEE Int. Conf. on Robotics and Animation pp . 2465-2470.
Ganguly et al. (2009) "*Emergence of a stable cortical map for neuroprosthetic control*," PLoS Bio., 7:e1000153 (13 pages).
Georgopoulos et al. (2005) "*Magnetoencephalographic signals predict movement trajectory in space*," Exp. Brain Res., 167:132-135.
Gourtzelidis et al. (2001) "*Systematic errors of planar arm movements provide evidence for space categorization effects and interaction of multiple frames of reference*," Exp. Brain Res., 139:59-69.
Hammon et al. (2008) "*Predicting reaching targets from human EEG*," IEEE Signal Proc. Mag., 25:69-77.
Hochberg et al (2006) "*Neuronal ensemble control of prosthetic devices by a human with tetraplegia*," Nature, 442:164-171.
Iacoboni et al. (2006) "*The mirror neuron system and the consequences of its dysfunction*," Nat. Rev. Neurosci., 7:942-951.
Jerbi et al. (2007) "*Coherent neural representation of hand speed in humans revealed by MEG imaging*," Proc. Natl. Acad. Sci. USA, 104:7676-7681.

Kelso et al. (1998) "*Dynamic cortical activity in the human brain reveals motor equivalence*," Nature, 392:814-818.
Kim et al (2008) "*Neural control of computer cursor velocity by decoding motor cortical spiking activity in humans with tetraplegia*," J. Neural Eng., 5:455-476.
Kim et al. (2006) "*A comparison of optimal MIMO linear and nonlinear models for brain-machine interfaces*," J. Neural Eng., 3:145-161.
Kubanek et al. (2009) "*Decoding flexion of individual fingers using electrocorticographic signals in humans*," J. Neural Eng., 6(6): 66001.
Lebedev et al. (2006) "*Brain-machine interfaces: past, present and future*," Trends Neurosci., 29:536-546).
Mellinger et al. (2007) "*An MEG-based brain-computer interface (BCI)*," Neuroimage, 36:581-593.
Miall (2003) "*Connecting mirror neurons and forward models*," NeuroReport, 14:2135-2137.
Miller et al. (2010) "*Cortical activity during motor execution, motor imagery, and imagery-based online feedback*," Proc. Natl. Acad. Sci. USA, 107:4430-4435.
Moran et al. (1999) "*Motor cortical activity during drawing movements: population representation during spiral tracing*," J. Neurophysiol., 82:2693-2704.
Mulliken et al. (2008) "*Decoding trajectories from posterior parietal cortex ensembles*," J. Neurosci., 28:12913-12926.
Nef et al. (2007) "*ARMin—exoskeleton for arm therapy in stroke patients*," Proc. IEEE Int. Conf. on Robotics and Animation, Noordwijk : 68-74.
Pascual-Marqui (2002) "*Standardized low-resolution brain electromagnetic tomography (sLORETA): technical details*," Methods Find Exp. Clin. Pharmacol 16 pages.
Perry et al. (2009) "*Mirror activity in the human brain while observing hand movements: a comparison between EEG desynchronization in the mu-range and previous fMRI results*," Brain Res., 1282:126-132.
Pistohl et al. (2008) "*Prediction of arm movement trajectories from ECoG-recordings in humans*," J. Neurosci. Methods, 167:105-114.
Reza Fazel-Rezai (2010) "Recent Advances in Brain-Computer Interface Systems" Intech open (234 pages).
Rosen et al. (2005) "*The human arm kinematics and dynamics during daily activity—toward a 7 DOF upper limb powered exoskeleton*," Int. Conf. On Advanced Robotics (ICAR), Seattle 8 pages.
Rossignol et al. (2007) "*Spinal cord injury: time to move?*," J. Neurosci., 27:11782-11792.
Sanchez et al. (2004) "*Ascertaining the importance of neurons to develop better brain-machine interfaces*," IEEE Trans. Biomed. Eng., 51:943-953.
Sanchez et al. (2008) "*Extraction and localization of mesoscopic motor control signals for human ECoG neuroprosthetics*," J. Neurosci. Methods, 167:63-81.
Sandwell D.T. (1987) "*Biharmonic spline interpolation of GEOS-3 and SEASAT altimeter data*". Geophys. Res. Lett. 2:139-142.
Schalk et al. (2007) "*Decoding two-dimensional movement trajectories using electrocorticographic signals in humans*," J. Neural. Eng., 4:264-275.
Schalk et al. (2008) "*Two-dimensional movement control using electrocorticographic signals in humans*," J. Neural Eng., 5:75-84.
Schalk G. et al. (2004) "*BCI2000 a general purpose brain-computer interface (BCI) system* " IEEE Trans. Biomed. Eng. 51:1034-43.
Schwartz et al. (2004) "*Differential representation of perception and action in the frontal cortex*," Science, 303:380-383.
Schwartz et al. (2006) "*Brain-Controlled Interfaces: Movement Restoration with Neural Prosthetics*" Neuron 52:205-220.
Scivoletto et al. (2008) "*Prediction of walking recovery after spinal cord injury*," Brain Res. Bull., 78:43-51.
Serruya et al. (2002) "*Instant neural control of a movement signal*," Nature, 416:141-142.
Taylor et al. (2002) "*Direct cortical control of 3D neuroprosthetic devices*," Science, 296:1829-1832.
Tkach et al. (2007), "*Congruent activity during action and action observation in motor cortex*," J. Neurosci. 27:13241-13250.

(56) References Cited

OTHER PUBLICATIONS

Tkach et al. (2008) "*Observation-based learning for brain-machine interfaces,*" Curr. Opin. Neurobiol., 18:589-594.
Truccolo et al. (2008) "*Primary motor cortex tuning to intended movement kinematics in humans with tetraplegia,*" J. Neurosci., 28:1163-1178.
Vargas-Irwin C.E. et al. (2010) "*Decoding Complete Reach and Grasp Actions form Local Primary Motor Cortex Population*" Journal of Neuroscience 30(29):9659-9669.
Velliste et al. (2008) "*Cortical control of a prosthetic arm for self-feeding,*" Nature, 453:1098-1101.
Venkatasubramanian V. (2009) "*Non Invasive Brain Computer Interface for Movement Control*" Proceedings of the World Congress on Engineering and Computer Science 1(5pages).
Vogt et al. (2007) "*Prefrontal involvement in imitation learning of hand actions: effects of practice and expertise,*" NeuroImage, 37:1371-1383.
Wahnoun et al (2006) "*Selection and parameterization of cortical neurons for neuroprosthetic control,*" J. Neural Eng., 3:162-171.
Waldert et al. (2008) "*Hand movement direction decoded from MEG and EEG,*" J. Neurosci., 28:1000-1008.
Wang W. et al. (2010) "*Decoding and Cortical Source Localization for Intended Movement Direction with MEG*" J. Neurophysiol. 104:2451-2461.
Wessberg et al. (2000) "*Real-time prediction of hand trajectory by ensembles of cortical neurons in primates,*" Nature, 408:361-365.
Wolpaw et al. (2004) "*Control of a two-dimensional movement signal by a noninvasive brain-computer interface in humans,*" Proc. Natl. Acad. Sci. USA, 101:17849-17854.
Wu et al. (2006) "*Evidence against a single coordinate system representation in the motor cortex,*" Exp. Brain Res., 175:197-210.
Wu et al. (2007) "*Coordinate system representations of movement direction in the premotor cortex,*" Exp. Brain Res., 176:652-657.
Yogev-Seligmann et al. (2008) "*The role of executive function and attention in gait,*" Mov. Disord. 23:329-342, quiz 472.
Zhuang J. et al. (2010) "*Decoding 3-D reach and grasp kinematics from high frequency local field potentials in primate primary motor cortex*" IEEE transactions on bio medical engineering 57(7):1774-84.
International Search Report (PCT/US2011/035299; Aug. 22, 2011).
Gu et al. (2009) "*Offline identification of imagined speed of wrist movements in paralyzed ALS patients from single-trial EEG,*" Front Neuroprosth. 1:1-7.

\* cited by examiner

TIME DOMAIN-BASED METHODS FOR NONINVASIVE BRAIN-MACHINE INTERFACES

CROSS-REFERENCE TO RELATED APPLICATIONS

This application is based on U.S. Patent Application Ser. No. 61/331,664, filed May 5, 2010, and U.S. Patent Application Ser. No. 61/369,128, filed Jul. 30, 2010, which applications are both incorporated herein by reference in their entireties and to which priority is claimed.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of N000140910126 awarded by the Office of Naval Research.

FIELD OF THE INVENTION

The present invention relates to brain computer interface systems which continuously decode observed, intended or self-generated movements from non-invasively acquired neural signals.

BACKGROUND OF THE INVENTION

Developments in the fields of robotic prosthesis have made it possible to build devices that mimic a human in its ability to manipulate multiple degrees of freedom simultaneously (e.g., the modular prosthetic limb developed by the Johns Hopkins University Army Physical Laboratories). However, designing strategies to control such prostheses, especially from neural activity, remains a challenge. Such a synergy between the hardware and its control using thought poses immense benefits for medical, rehabilitation and motor performance enhancements.

The field of brain computer interface (BCI) systems or brain machine interface (BMI) systems deals with interpreting the neural code and generating commands to control an assistive device. The terms brain computer interface (BCI) and brain machine interface (BMI) are used interchangeably herein. BCI systems may thus potentially provide movement-impaired persons with the ability to interact with their environment using only their thoughts to control assistive devices such as communication programs and smart artificial arms. Some BCI systems rely on neural signals acquired noninvasively with electroencephalography (EEG) (Wolpaw et al. (2004) "*Control of a two-dimensional movement signal by a noninvasive brain-computer interface in humans*," Proc. Natl. Acad. Sci. USA, 101:17849-17854), while other BCI systems acquire signals invasively with electrocorticography (ECoG) (Schalk et al. (2008) "*Two-dimensional movement control using electrocorticographic signals in humans*," J. Neural Eng., 5:75-84) or microelectrode arrays seated into cortical tissue (Hochberg et al (2006) "*Neuronal ensemble control of prosthetic devices by a human with tetraplegia*," Nature, 442:164-171).

Invasive BCI systems typically acquire neural signals with intracranial or subdural electrodes, while noninvasive BCI systems typically acquire neural signals with scalp EEG. Some drawbacks of invasive BCI systems are the inherent risks of surgery and gradual degradation of signal integrity. However, a limitation of conventional noninvasive BCI systems for two-dimensional control of a cursor, in particular those based on sensorimotor rhythms, is the lengthy training time required by users to achieve satisfactory performance.

With regard to invasive systems, researchers have extracted hand trajectories or velocity profiles from neuronal signals acquired with electrodes seated directly into cortical tissue and, in some cases, used these kinematics to command a robotic arm in real time (Wessberg et al. (2000) "*Real-time prediction of hand trajectory by ensembles of cortical neurons in primates*," Nature, 404:361-365; Serruya et al. (2002) "*Instant neural control of a movement signal*," Nature, 416:141-142; Taylor et al. (2002) "*Direct cortical control of 3D neuroprosthetic devices*," Science, 296:1829-1832; Hochberg et al (2006), supra, Nature, 442:164-171; Kim et al. (2006) "*A comparison of optimal MIMO linear and nonlinear models for brain-machine interfaces*," J. Neural Eng., 3:145-161; Mulliken et al. (2008) "*Decoding trajectories from posterior parietal cortex ensembles*," J. Neurosci., 28:12913-12926; Truccolo et al. (2008) "*Primary motor cortex tuning to intended movement kinematics in humans with tetraplegia*," J. Neurosci., 28:1163-1178; Velliste et al. (2008) "*Cortical control of a prosthetic arm for self-feeding*," Nature, 453:1098-1101). Investigators have also extracted hand kinematics from intracranial local field potentials obtained through less invasive ECoG (Schalk et al. (2007) "*Decoding two-dimensional movement trajectories using electrocorticographic signals in humans*," J. Neural. Eng., 4:264-275; Pistohl et al. (2008) "*Prediction of arm movement trajectories from ECoG-recordings in humans*," J. Neurosci. Methods, 167:105-114; Sanchez et al. (2008) "*Extraction and localization of mesoscopic motor control signals for human ECoG neuroprosthetics*," J. Neurosci. Methods, 167:63-81).

However, little work has been done to continuously decode natural, multi-joint limb kinematics from neural signals acquired noninvasively. Only a few studies report continuous decoding of two-dimensional (2D) hand and tool kinematics from magnetoencephalography (MEG) (Georgopoulos et al. (2005) "*Magnetoencephalographic signals predict movement trajectory in space*," Exp. Brain Res., 167:132-135; Jerbi et al. (2007) "*Coherent neural representation of hand speed in humans revealed by MEG imaging*," Proc. Natl. Acad. Sci. USA, 104:7676-7681; Bradberry et al (2008) "*Decoding hand and cursor kinematics from magnetoencephalographic signals during tool use*," Conf. Proc. Eng. Med. Biol. Soc. 2008:5306-5309; Bradberry et al. (2009a) "*Decoding center-out hand velocity from MEG signals during visuomotor adaptation*," Neuro-image, 47:1691-1700). However, such MEG systems are immobile and therefore unsuitable for practical BCI systems.

Researchers have not demonstrated continuous decoding of limb kinematics from EEG-based systems. Instead, most EEG studies have discretely classified the direction/speed of 2D hand/wrist movements or different motor imagery tasks on a single-trial basis (Mellinger et al. (2007) "*An MEG-based brain-computer interface (BCI)*," Neuroimage, 36:581-593; Hammon et al. (2008) "*Predicting reaching targets from human EEG*," IEEE Signal Proc. Mag., 25:69-77; Walden et al. (2008) "*Hand movement direction decoded from MEG and EEG*," J. Neurosci., 28:1000-1008; Gu et al. (2009) "*Offline identification of imagined speed of wrist movements in paralyzed ALS patients from single-trial EEG*," Front Neuroprosth. 1:1-7) or they have demonstrated 2D continuous control of a cursor through biofeedback training (Wolpaw et al. (2004), supra, Proc. Natl. Acad. Sci.

USA, 101:17849-17854). The lack of attention to reconstructing kinematics of natural limb (e.g. hand) movements from EEG is due in part because researchers consider training subjects to modulate EEG activity, independent of reconstructing hand kinematics, suffices for 2D control (Wolpaw et al. (2004), supra, Proc. Natl. Acad. Sci. USA, 101:17849-17854). Further, it is generally thought that the signal-to-noise ratio, the bandwidth, and the information content of neural data acquired via noninvasive scalp EEG are insufficient to extract sufficiently detailed information about natural, multi-joint movements of the upper limb (Lebedev et al. (2006) "*Brain-machine interfaces: past, present and future,*" Trends Neurosci., 29:536-546).

Current noninvasive EEG-based BCI systems for 2D cursor control require subjects to learn how to modulate specific frequency bands of neural activity, i.e. sensorimotor rhythms, to move a cursor to acquire targets (Wolpaw et al. (2004), supra, Proc. Natl. Acad. Sci. USA, 101:17849-17854). These types of studies based on sensorimotor rhythms require weeks to months of training before satisfactory levels of performance are attained. Relative to EEG signals, the increased signal-to-noise ratio and bandwidth of invasively acquired neural data are commonly thought to be factors that reduce the training time required by users of invasive BCI systems (Schalk et al. (2008), supra, J. Neural Eng., 5:75-84). In addition, studies of tetraplegic humans with implanted microelectrode arrays have exclusively demonstrated 2D control of a cursor through imagined natural movement (Hochberg et al (2006), supra, Nature, 442:164-171; Kim et al (2008) "*Neural control of computer cursor velocity by decoding motor cortical spiking activity in humans with tetraplegia,*" J. Neural Eng., 5:455-476). This decoding of imagined natural movement is also a likely factor in reduced training time since neural signals directly correlate with intended actions.

Traditionally, the focus for many researchers of decoding movement intent from neural activity has been on decoding the desired hand position (Carmena et al. (2003) "*Learning to control a brain-machine interface for reaching and grasping by primates,*" PLoS Biol., 1, E42; Bradbery et al. (2010) "*Reconstructing three-dimensional hand movements from noninvasive electrocephalographic signals,*" J. Neurosci. 30:3432-3437; Georgopoulos et al. (2005), supra, Exp. Brain Res., 167:132-135; Hochberg et al (2006), supra, Nature, 442:164-171; Schalk et al. (2007), supra, J. Neural. Eng., 4:264-275; Velliste et al. (2008), supra, Nature, 453: 1098-1101; Wessberg et al. (2000), supra, Nature, 404:361-365; Walden et al. (2008), supra, J. Neurosci., 28:1000-1008). The problem of decoding hand gestures, which involves simultaneously decoding multiple finger joint angles, is relatively complex due to the many degrees of freedom involved. Researchers have only recently started investigating the possibility of deciphering finger movement and simple open/close hand movements (Acharya et al. (2010) "*Electrocorticographic amplitude predicts finger positions during slow grasping motions of the hand,*" J. Neural Eng., 7(4):46002; Kubanek et al. (2009) "*Decoding flexion of individual fingers using electrocorticographic signals in humans,*" J. Neural Eng., 6(6): 66001). Moreover, the methods used in many prior studies have involved invasive procedures required to measure neural signals. Other studies have indicated that, in the case of noninvasive EEG signals, signal averaging must be used over many movement attempts to extract a usable signal and the extracted signal cannot be employed to reproduce a time-varying arm trajectory.

More recently, some advancements have been made in the development of wearable robots or "exoskeletons" for medical (e.g., restoration of walking and running after spinal cord injury, amyotrophic lateral sclerosis or traumatic brain injury to name a few), rehabilitation training (e.g., assistive or resistive movement therapies), and motor performance enhancement applications in which the exoskeletons are not being permanently integrated with the body. Such exoskeletons evolved directly from orthotic devices worn on the arm or leg to provide assistive movement for specific joints such as the elbow or knee.

Exoskeletons range from powered versions of these orthotic devices to full body suits designed for augmenting the strength and load-carrying capability of able individuals. In addition, exoskeletons are finding their way into rehabilitation therapy, as they can provide either assistance or resistance in patient conditions ranging from full incapacitation (e.g., immediate post-stroke or traumatic brain injury) to almost full-strength following weeks of therapy. While the evolution of exoskeleton hardware has proceeded at a rapid pace, controlling these devices has lagged significantly behind.

Most exoskeletons use force sensors mounted at the handle or along attach points on the limbs to generate commands to move the exoskeleton in the appropriate direction (Carignan et al. (2008) "*Controlling shoulder impedance in a rehabilitation arm exoskeleton,*" proc. IEEE Int. Conf. on Robotics and Automation (ICRA), Pasadena, 2453-2458; Frisoli et al. (2008) "*Robot mediated arm rehabilitation in virtual environments for chronic stroke patients: a clinical study,*" Proc. IEEE Int. Conf. on Robotics and Animation, Pasadena, 2465-2470; Nef et al. (2007) "*ARMin—exoskeleton for arm therapy in stroke patients,*" Proc. IEEE Int. Conf. on Robotics and Animation, Noordwijk, The Netherlands, 68-74). However, such devices are not scalable as a human-machine solution for minimizing the time between thought and action as well as for patients with severe injuries who need some assistance just to lift or move their limbs.

Some researchers have investigated using (non-invasive) surface electromyography (sEMG) as an alternative way to decipher user intent (Rosen et al. (2005) "The human arm kinematics and dynamics during daily activity—toward a 7 DOF upper limb powered exoskeleton," Int. Conf. on Advanced Robotics (ICAR), Seattle). In one strategy, non-invasive electrodes pick up signals from muscles that generate elbow flexion/extension, which are then processed by software to command movement of the elbow orthosis. The human then closes the loop through visual and proprioceptive feedback during the movement. Unfortunately, this strategy has fails to work for patients with severe motor impairment who do not generate enough neuromuscular activity to be captured by sEMG. Moreover, sEMG patterns are severely compromised by neurological disease, injury or noise during movement rendering them difficult to decode accurately.

Thus, brain computer interfaces (BCIs), or brain machine interfaces (BMIs) pose the best avenue to effective control of exoskeletons since it is a user's thought that commands motion. Bioengineers have had some success with using electrodes implanted in a monkey's brain to command motion of a robotic arm and gripper (Velliste et al. (2008), supra, Nature, 453:1098-1101). Bipedal locomotion control is of great interest to the field of BCIs. Since locomotion deficits are commonly associated with spinal cord injury (Scivoletto et al. (2008) "*Prediction of walking recovery after spinal cord injury,*" Brain Res. Bull., 78:43-51; Rossignol et al. (2007) "*Spinal cord injury: time to move?*," J. Neurosci., 27:11782-11792) and neurodegenerative diseases (Boonstra et al. (2008) "*Gait disorders and balance disturbances in Parkinson's disease: clinical update and pathophysiology*," Curr. Opin. Neurol., 21:461-471; Yogev-Seligmann et al. (2008) "*The role of executive function and attention in gait*," Mov. Disord. 23:329-342, quiz 472), there is a need to investigate new potential therapies to restore gait control in such patients. While the feasibility of a BMI for upper limbs has been demonstrated in studies in monkeys (Carmena et al. (2003), supra, PLoS Biol., 1, E42; Velliste et al. (2008), supra, Nature, 453:1098-1101) and humans (Hochberg et al (2006), supra, Nature, 442:164-171; Bradberry et al. (2010), supra, J. Neurosci. 30:3432-3437), neural decoding of bipedal locomotion in humans has not yet been demonstrated. Recently, bipedal locomotion patterns were reconstructed from cortical ensemble activity in Rhesus monkeys recorded with implanted electrode arrays (Fitzsimmons et al. (2009) "*Extracting kinematic parameters for monkey walking from cortical neuronal ensemble activity*," Front. Integr. Neurosic., 3:3 doi: 10.3389/neuro.07.003.2009). However, such invasive technology is not likely to be an acceptable solution for exoskeletons for use by humans.

SUMMARY OF THE INVENTION

The present invention is directed to a BCI system that continuously decodes observed, imagined or actual movements from EEG signals with substantially reduced training time by a subject. The acquired signals may be utilized in a BCI system or a brain machine interface (BMI) for controlling a machine. The term machine as used herein refers to a device, tool or mechanism designed to serve a specific purpose or goal. Thus a machine may be a computer cursor on a display screen (e.g., as provided in a BCI), a robotic limb (e.g., a hand, arm or leg), a motorized wheelchair, a videogame, a digital phone, a switch, an automobile, or a motorized assistive device.

For example, using the disclosed noninvasive BCI system and observational learning, subjects were able to accomplish two-dimensional control of a cursor with performance levels comparable to those of invasive BCI systems. Compared to other studies of noninvasive BCI systems, training time was substantially reduced, requiring only a single session of decoder calibration (~20 minutes) and subject practice (~20 minutes). Further, standardized low-resolution brain electromagnetic tomography was utilized to reveal that the neural sources that encoded observed cursor movement may implicate a human mirror neuron system (MNS). These findings offer the potential to continuously control complex devices such as robotic arms with one's mind without lengthy training or surgery.

According to one aspect of the present invention, a noninvasive BCI system is provided that utilizes a decoding method during a single session lasting less than 2 hours and that requires only brief training. It is believed that the putative human MNS, which predicts and interprets a subject's actions and the actions of others (Tkach et al. (2008) "*Observation-based learning for brain-machine interfaces*," Curr. Opin. Neurobiol., 18:589-594), may be exploited during training by asking subjects to combine motor imagery with observation of a video of cursor movement. It is further believed that a neural decoder may subsequently be built off-line that would predict cursor movement from neural activity. The decoder could then be used on-line for real-time brain-control of cursor movement with little training time. The involvement of neural regions was examined in encoding cursor velocity during observation of computer-controlled cursor movement and during tasks requiring a brain-controlled cursor to acquire targets in two dimensional space.

According to another aspect of the present invention, a noninvasive BMI system is provided that decodes the kinematics of natural hand movements from EEG signals. The disclosed method controls each degree of freedom in a prosthetic or orthotic device by simultaneously decoding multiple desired kinematic parameters from multi-channel noninvasive neural activity. The decoded signals thus serve as new signals for controlling neuromotor prostheses. Hand velocity was continuously extracted from signals collected during a three-dimensional (3D) center-out reaching task. To assure a realistic task, subjects were not cued. Rather, the subjects chose which target to acquire and when to initiate movement. Since EEG coupled with our decoding method facilitated the investigation of sensor contributions to decoding with high temporal resolution, the location of salient sensors across time lags was examined. Using standardized low-resolution brain electromagnetic tomography (sLORETA) (Pascual-Marqui (2002), supra, Methods Find Exp. Clin. Pharmacol., 24 (Suppl D): 5-12), the sources most involved in encoding hand velocity were estimated. Moreover, the relationship between decoding accuracy and movement variability was investigated.

According to one disclosed method, hand movement intentions are deciphered from neural data streams in humans. The inputs to the method include neural signals from the human brain in the form of noninvasive (EEG or MEG) or invasive (ECoG and multi-unit activity) data, and the outputs are the desired kinematic parameter trajectories (e.g., finger joint angles and velocities). The decoded outputs may be used to simultaneously control multiple degrees of freedom in a prosthetic or orthotic hand for medical (e.g., regaining hand function after an upper-limb amputation, atrophy, or paralysis), rehabilitation training (e.g., assistive or resistive movement therapies), and motor performance enhancement (e.g., remote control of robotic actions) applications in which an exoskeleton is not being permanently integrated with the body. Moreover, as the neural signals acquired noninvasively using scalp electroencephalography (EEG) and processed according to the disclosed methods in this invention are correlated with meaningful behavioral variables (e.g., sequence of spatial positions or spatial configurations of hand joint angles during grasping), confluence between the brain and the exoskeleton may be achieved. Thus, the disclosed method for noninvasive decoding of human (multi-joint) hand gesture patterns from noninvasive scalp EEG signals alone can achieve BMI confluence.

According to another aspect of the present invention, a noninvasive BMI system is provided that decodes the kinematics of human bipedal locomotion from EEG signals. The desired decoded signals, such as the predicted joint positions of the lower extremities, may be utilized for the control of wearable lower-limb robots or "exoskeletons" for medical (e.g., for restoration of walking and running after spinal cord injury, amyotrophic lateral sclerosis or traumatic brain injury), rehabilitation training (e.g., assistive or resistive movement therapies), and motor performance enhancement (e.g. military or industrial) applications in which the exoskeletons are not being permanently integrated with the body. In another implementation, the decoded neural signals may be utilized to remotely control a robot (e.g., a walking robot). Moreover, as the neural EEG signals are acquired and processed according to the disclosed methods, such data may be correlated with meaningful behavioral variables (e.g., sequence of spatial positions or spatial configurations of legs during walking), and confluence between the brain and the exoskeleton may be achieved. Thus, the disclosed methods for noninvasive decoding of human (multi-joint) bipedal locomotion patterns from noninvasive scalp EEG signals alone may achieve brain-machine confluence.

A noninvasive brain computer interface (BCI) system according to an embodiment of the present invention includes an electroencephalography (EEG) electrode array configured to acquire EEG signals generated by a subject, wherein the subject is observing movement of a stimulus, and a computer coupled to the EEG electrode array and configured to collect and process the acquired EEG signals. The computer utilizes a decoding algorithm that continuously decodes neural activity associated with the observed movement to determine an intent of the subject.

In one implementation, the decoding algorithm extracts and analyzes lower frequency brain waves from a plurality of EEG electrodes during the continuous decoding. Further, the decoding algorithm extracts and analyzes neural activity in the time domain during the continuous decoding.

In one implementation, the system includes a display operably coupled to the computer. The computer generates commands to control two-dimensional movement of a cursor displayed on the display in response to EEG signals generated by the subject.

In another implementation, the system includes a prosthetic device operably coupled to the computer. The computer generates commands to control three-dimensional movement of the prosthetic device in response to EEG signals generated by the subject. In some embodiments, the prosthetic device includes a plurality of sensors, which record three-dimensional kinematics of movement of the prosthetic device. The computer synchronizes the acquired EEG signals with the recorded three-dimensional kinematics to continuously decode the neural activity.

In another implementation, the subject simultaneously imagines movement of a limb tracking the observed movement. The decoded neural activity is associated with the observed movement in combination with the imagined movement.

In another implementation, EEG signals acquired from a portion of sensors of the EEG electrode array are rejected by the decoding algorithm based on contribution percentage of neural activity sensed.

A method of decoding neural activity for a brain computer interface (BCI) system according to an embodiment of the present invention includes the steps of: recording electroencephalography (EEG) signals of a subject when the subject observes movement of a stimulus while the subject is simultaneously imagining movement of a limb tracking the movement of the stimulus; and continuously decoding multi-channel neural activity associated with the observed movement and the imagined movement to determine an intent of the subject.

In one implementation, the disclosed method includes a further step of generating command signals for controlling movement of a device operably associated with the BCI system. The command signals are associated with the intent of the subject.

In another implementation, the device is a cursor displayed on a display. The cursor is movable in two-dimensions on the display based on EEG signals of the subject. In another implementation, the device is a prosthetic device movable in three-dimensions based on EEG signals of the subject.

A BCI system according to another embodiment includes an EEG electrode array configured to acquire EEG signals generated by a subject, and a neural decoder calibrated using biologically-generated movement for the purposes of controlling the BCI system.

A method of identifying a neural biomarker of a movement condition according to another aspect of the present invention includes the steps of: recording electroencephalography (EEG) signals of a subject when the subject observes movement of a stimulus while the subject is simultaneously imagining movement of a limb tracking the movement of the stimulus; continuously decoding neural activity associated with the observed movement and the imagined movement to determine a biomarker of a movement condition. In one implementation, the movement condition is associated with a movement disorder due to a neurological condition, a developmental disorder, or abnormal aging.

A noninvasive BCI system according to another aspect of the present invention continuously decodes neural activity of imagined natural movements in at least two dimensions. In one implementation, the decoded neural activity is associated with natural hand movement in a human subject. In another implementation, the decoded neural activity is associated with bipedal movement in a human subject.

A noninvasive BCI system according to another aspect of the present invention continuously decodes imagined or actual movements from EEG signals with substantially reduced training time by a subject. In one implementation, the system decodes neural activity of movements in at least two dimensions.

Thus, the disclosed inventions have wide ranging applications. In one embodiment, the methods disclosed may be utilized to restore hand motor function in amputees or patients with stroke by controlling an artificial arm via our noninvasive BMI system. In another embodiment, the disclosed methods may be used to control a motorized wheelchair by decoding movement intention from the user (e.g., left versus right turn, move forward versus backwards). In another embodiment, the disclosed methods may serve to extract noninvasive biomarkers, at the macro-scale afforded by EEG, of movement disorders due to neurological disease, developmental disorders or abnormal aging. According to another embodiment, the disclosed methods may be used to control (hands-free) gaming and virtual reality applications.

DETAILED DESCRIPTION OF THE INVENTION

Figure 1:
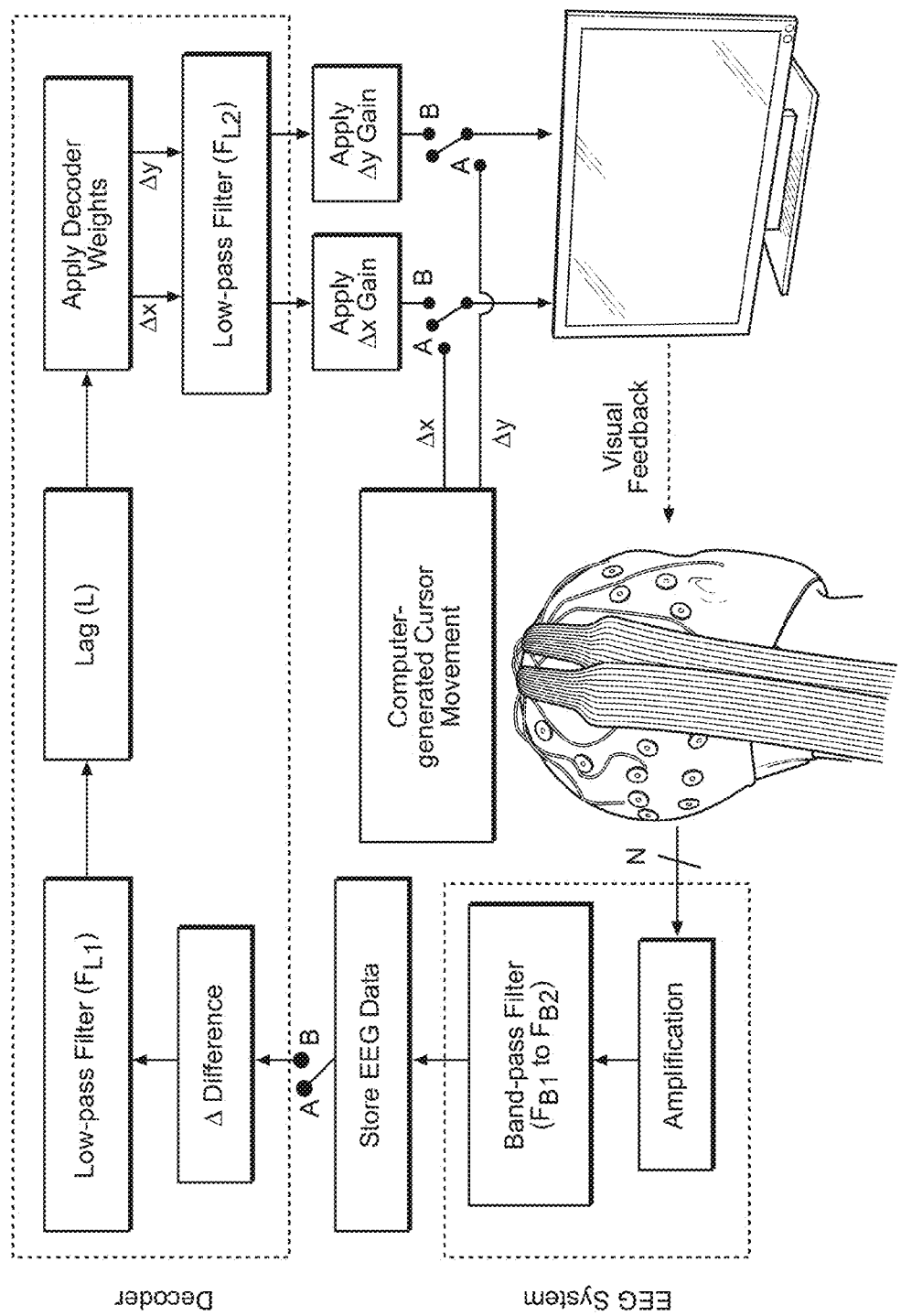
FIG. 1 illustrates a setup of an EEG-based BCI system according a first embodiment of the present invention. A subject's EEG signals were acquired while sitting in a chair facing a monitor that displayed a cursor and targets (only target acquisition phase). During the calibration phase, subjects observed a computer-controlled cursor to collect data for subsequent initialization of the decoder. In the target acquisition phase, the subject moved the brain-controlled cursor to acquire targets that appeared at the left, top, right, or bottom of the computer screen.

A noninvasive BCI system according to a first embodiment of the present invention substantially reduces the training time required by a user to achieve satisfactory multidimensional control of a cursor on a display. The disclosed BCI system is an EEG-based system that employs continuous decoding of imagined continuous finger, hand or arm movements. The system requires only a single session of decoder calibration and subject practice (totaling approximately 40 minutes) before a subject can effectively operate the system and achieve satisfactory results.

The disclosed BCI system is beneficial for movement impaired persons, given the decoder calibration and/or subject training procedures do not require overt movement by the subject. For this reason, a decoder calibration procedure was utilized that requires only observation of biologically plausible cursor movement. This type of training for BCI systems presumably engages the MNS, which predicts and interprets one's own actions and the actions of others (Tkach et al. (2008), supra, Curr. Opin. Neurobiol., 18:589-594). In fact, neuronal activity acquired from intracortical microelectrode arrays implanted in the dorsal premotor cortex (PMd) and the arm area of the PrG (primary motor cortex, M1), common sites for BCI-related studies, exhibit qualities of mirror neurons during observation of cursor movements (Cisek et al. (2004), supra, Nature, 431:993-996; Wahnoun et al (2006), supra, J. Neural Eng., 3:162-171; Tkach et al. (2007), "*Congruent activity during action and action observation in motor cortex*," J. Neurosci. 27:13241-13250).

According to certain aspects of the invention, the disclosed methods and systems acquire noninvasively EEG signals. Further, the disclosed methods and systems utilize the EEG signals in the delta band (<4 Hz), and in the time domain. Neural activity may be uniquely encoded in the time domain or in the frequency domain. The acquired signals in the time domain are uniquely processed and analyzed according to the disclosed decoding algorithms. Thus, the disclosed decoding algorithms are specific to decoding data in the time domain. Thus, the utilization of this combination of features (noninvasively acquired EEG signals in the delta band and in the time domain) is unique compared to conventional systems and methods.

Thus, the disclosed methods and systems differ from conventional systems in that the disclosed decoding methods: are not based on the extraction and analysis of features in the frequency domain; do not use the power in specific frequency bands of specific signals as the independent variables used to control a cursor on a video monitor or other device; do not require neurofeedback training to learn to modulate the brain rhythms, and do not require extensive subject training (e.g., several runs or sessions requiring weeks to months) to attain reasonable task performance.

Further, the disclosed methods and systems: do not require invasive techniques for accessing the brain signals; are not based on the extraction and analysis of higher frequency brain waves in the gamma band (>40 Hz); and are not based on finding correlation between specific power changes in the gamma band and specific behavioral conditions. Rather, the disclosed methods extract and analyze, in the time-domain, lower-frequency brain waves in the delta band (<4 Hz).

According to certain embodiments, imagined movements from EEG signals were continously decoded in a BCI experiment involving five subjects. The procedure involved three phases: calibration, user practice, and target acquisition.

During the calibration phase, subjects imagined moving their right arm and/or finger tracking a cursor that moved in two dimensions on a computer screen for approximately 10 minutes. A decoding initialization procedure was then executed to find the decoder parameters that best mapped 34 EEG signals to observed horizontal and vertical cursor velocities (~10 minutes). Through subsequent investigation of the cortical sources that encoded for observed cursor velocity, a large neural network that comprised brain regions considered a part of the human MNS was engaged.

During the practice phase, after an initial manual adjustment of cursor speed to comfortable values by investigators (~10 minutes), subjects used the calibrated decoder to move the cursor with their thoughts in two dimensions as desired without task constraints for 10 minutes.

During the target acquisition phase, subjects used their thoughts to move the cursor to a target that appeared pseudorandomly at the top, bottom, left, or right side of the display. If subjects did not acquire the target within about 15 seconds, the trial was aborted and a new target appeared on the screen. Four 10-minute runs of target acquisition were performed. The mean standard error (SE) of the target hit rate was 73±4% across subjects and runs.

A snapshot of cortical sources that maximally encoded for cursor velocity during the target acquisition phase primarily differed from that of the calibration phase by revealing a more widespread involvement of the primary sensorimotor cortex and decreased involvement of the putative MNS. Our results indicates that the disclosed procedure of continuously decoding imagined movements from EEG signals substantially reduces training time for cursor control in a noninvasive BCI system, and allows for unique insights into the cortical regions involved in encoding imagined and observed movements under different task constraints. Moreover, our decoding method serves as a novel tool for further study of the development and plasticity of neural representations underlying action observation and action production at the macroscale afforded by EEG.

An example experiment of an EEG-based BCI system according to a first embodiment is provided:

EXAMPLE 1

Methods and Materials

Five healthy, right-handed subjects performed a three-phase task: calibration, practice, and target acquisition. None of the subjects had previously participated in a BCI study. In all phases, the subjects EEG signals were acquired while they sat upright in a chair with hands resting in their laps at arm's length away from a computer monitor that displayed a workspace of dimensions 30×30 cm and a cursor of diameter 1.5 cm (0.20% of workspace). The subjects were instructed to remain still and relax their muscles to reduce the introduction of artifacts into the EEG recordings.

A diagram of data processing flow for the EEG-based BCI system according to the first embodiment is illustrated in FIG. 1. When the switches are in position A, the system is in an observation/calibration mode. In the observation/calibration mode, a subject observes a replay of a pilot subject's cursor movements on a computer screen while data from a plurality N (e.g. 34) of EEG sensors are continuously acquired by an EEG system. The EEG system amplifies and band-pass filters the signals acquired from the sensors from $F_{B1}$ (0.01) to $F_{B2}$ (30) Hz, and then stores the resulting EEG data. The stored EEG data and observed cursor velocity are then used to compute decoder weights.

When the switches are in position B, the system is in either a practice mode or a target acquisition mode. In the practice mode, after the EEG data has been stored, it is continuously temporally differenced, low-pass filtered at $F_{L1}$ (1) Hz, lagged L (11) times (a lag of 0 also occurs), decoded for cursor velocity by the calibrated decoder from the preceding calibration phase, low-pass filtered again at $F_{L2}$ (1) Hz, and gain adjusted. The data is then displayed on a computer display as visual feedback to the subject. The practice mode differs from the target acquisition mode in that, during practice, the gains preceding the cursor display are manually adjusted by investigators (although the gain setting may also be done automatically), and no targets are present on the screen. In the target acquisition mode, a subject attempts to move the cursor to a target that is displayed pseudorandomly at the left, right, top, or bottom of the display screen.

Data Acquisition

A 64-sensor cap for sensing EEG signals (e.g., such as available from Electro-Cap International Inc. of Eaton, Ohio) was placed on the head of each subject and in accordance with the extended International 10-20 system with ear-linked reference. The cap was used to collect 58 channels of EEG activity from each subject.

Continuous EEG signals were sampled at 100 Hz and amplified 1000 times via an amplifier and associated software (e.g., such as the Synamps I amplifier system and Neuroscan v4.3 software available from Compumedics Neuroscan of Charlotte, N.C.). Additionally, the EEG signals were band-pass filtered from 0.01 to 30 Hz.

Electrooccular (EOG) activity was measured with a bipolar sensor montage with sensors attached superior and inferior to the orbital fossa of the right eye for vertical eye movements and to the external canthi for horizontal eye movements. The EEG signals were continuously sent to a software BCI2000 software system (e.g., BCI2000, a general-purpose system for BCI research, data acquisition, stimulus presentation, and brain monitoring applications; see bci2000.org) for online processing and storage. BCI2000 was responsible for moving the cursor based on the decoder function (described below), which was integrated into the open source software system. BCI2000 was also responsible for storing cursor movement data as well as collecting markers of workspace events such as target acquisition.

Electromyographic (EMG) signals were amplified and collected at 2000 Hz from two bipolar surface electrodes over the flexor carpi radialis and extensor digitorum muscles of the right forearm using a wireless EMG system (e.g., the Aurion ZeroWire EMG system available from Biomechanics and Mechatronics of Karditsa, Greece) (10-1000 Hz bandwidth, constant electrode gain of 1000).

Calibration Phase

The calibration of the neural decoder did not require overt movement. Rather, the decoder was calibrated in a manner similar to that described in an invasive BCI study (see Bradberry et al. (2010), supra, J. Neurosci. 30:3432-3437; Hochberg et al (2006), supra, Nature, 442:164-171), and required only motor imagery during observation of cursor movement. In particular, the subjects were instructed to imagine using their finger to track biologically plausible movement of a computer-controlled cursor. The decoder was subsequently calibrated based on the cursor velocity and EEG signals.

During a 10 minute calibration phase, subjects were instructed to imagine moving their right arm and/or finger to track a computer-controlled cursor moving in two dimensions on a computer screen. The movements of the computer-controlled cursor were generated by replaying a pilot subject's brain-controlled cursor movements from a practice run by the pilot. The pilot subject did not participate as one of the five subjects in the study. However, the cursor movements replayed for the subjects were generated by the pilot subject during a previous target acquisition phase of the disclosed system. Accordingly, all movements replayed to the subjects were movements derived from acquired EEG data from the pilot subject.

Figure 2:
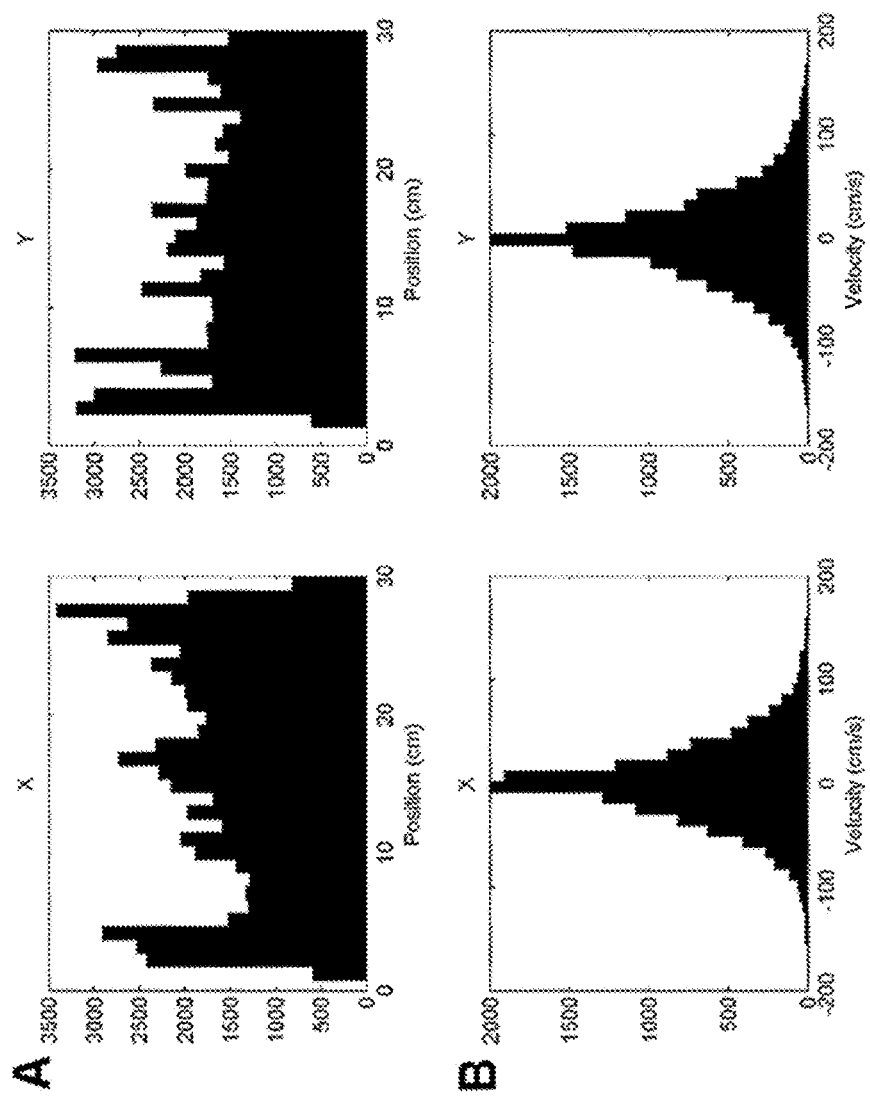
FIG. 2 are histograms of observed cursor kinematics during the calibration phase according to the first embodiment. As shown in Panel A, histograms of horizontal (left) and vertical (right) positions indicated approximately uniform coverage of the workspace. As shown in Panel B, histograms of horizontal (left) and vertical (right) positions inferred movements with bell-shaped velocity profiles, indicative of biological motion. The velocity histograms actual peak near 5000 but were truncated to view the shape of the base.

Histograms of observed cursor kinematics during the calibration phase are illustrated in FIG. 2. The histograms of horizontal and vertical positions and velocities of the computer-controlled movements indicate approximately uniform coverage of the display screen and biological motion, respectively. Referring to FIG. 2, Panel A, histograms of horizontal (left) and vertical (right) positions indicate approximately uniform coverage of the display screen workspace. Referring to FIG. 2, Panel B, histograms of horizontal (left) and vertical (right) positions inferred movements with bell-shaped velocity profiles, and are indicative of biological motion. (Note that the velocity histograms actually peaked near 5000, but are truncated in FIG. 2 in order to view the shape of the base).

The decoding procedure (described in further detail below) was then executed (~10 minutes of computation time) in order to calibrate the decoder so that it best mapped the EEG signals to observed horizontal and vertical cursor velocities. During pilot testing, it was discovered that asking subjects to visually fixate on the center of the display screen while simultaneously imagining their fingers or arms tracking the cursor burdened the subjects and compromised the decoding. Therefore, the subjects were instructed to freely move their eyes, but to maintain eye contact and spatial attention with the moving cursor on the display. The off-line decoding procedure was executed with channels of vertical and horizontal EOG activity included, and the percent contribution of these eye channels was accessed (shown in Table 2 below).

Practice Phase

During the practice phase, the subjects used the calibrated decoder to attempt to move the cursor with their thoughts in two dimensions as desired (without task constraints). The subjects were instructed to determine for themselves how to best control the cursor by exploring the display screen workspace. They were also informed as to where the target locations would be in the target acquisition phase that would follow. The subjects were again free to move their eyes during the practice phase. During the initial portion of the practice phase, horizontal and vertical gains were independently adjusted to balance cursor speed so that the velocity of the brain-controlled cursor was comfortably viewable to the subjects. After the gains were manually adjusted (~10 minutes), the subjects practiced moving the cursor without task constraints for approximately 10 minutes.

Target Acquisition

During the target acquisition phase, the subjects were instructed to use their thoughts to move the cursor in two dimensions on the display screen to reach a peripheral target (1.3% of workspace) that would appear pseudorandomly at the top, bottom, left, or right side of the screen. The subjects were informed that if the target was not acquired within 15 seconds after appearing on the screen, that target acquisition trial was considered a failure and a new target would then appear. Four 10-minute runs of target acquisition were performed with a 1-minute rest interval between each run.

Decoding Method

The decoding method employed is described in detail in Bradberry et al. (2010), supra, J. Neurosci. 30:3432-3437, the disclosure of which is incorporated herein by reference. First, a fourth-order, low-pass Butterworth filter with a cutoff frequency of 1 Hz was applied to the kinematic and EEG data. Next, the first-order temporal difference of the EEG data was computed. To continuously decode cursor velocity from the EEG signals, a linear decoding model was employed:

$$x[t] - x[t-1] = a_x + \sum_{n=1}^{N} \sum_{k=0}^{L} b_{nkx} S_n[t-k]$$

$$y[t] - y[t-1] = a_y + \sum_{n=1}^{N} \sum_{k=0}^{L} b_{nky} S_n[t-k]$$

where $x[t]-x[t-1]$ and $y[t]-y[t-1]$ are the horizontal and vertical velocities of the cursor at time sample t respectively, N is the number of EEG sensors, L (=11) is the number of time lags, $S_n[t-k]$ is the difference in voltage measured at EEG sensor n at time lag k, and the a and b variables are weights obtained through multiple linear regression.

Optimal sensors (N=34) for velocity reconstruction (e.g., such as disclosed in Bradberry et al. (2010), supra, J. Neurosci. 30:3432-3437) were used for the decoding method. For the calibration phase, a 10×10-fold cross-validation procedure was employed to assess the reconstruction accuracy of observed cursor velocity from EEG signals. In this procedure, the entire continuous data were divided into 10 parts, whereby 9 parts were used for training, and the remaining 1 part was used for testing. The cross-validation procedure was considered complete when each of the 10 combinations of training and testing data were exhausted, and the mean Pearson correlation coefficient (r) between measured and reconstructed kinematics was computed across folds. Prior to computing r, the kinematic signals were smoothed with a fourth-order, low-pass Butterworth filter with a cutoff frequency, of 1 Hz. For the ensuing practice and target acquisition phases, the regression weights (a and b variables) for the cross-validation fold with the highest r were used for online decoding.

Scalp Maps of Sensor Contributions

In order to graphically assess the relative contributions of scalp regions to the reconstruction of cursor velocity, the decoding procedure disclosed above was run on standardized EEG signals, and the across-subject mean of the magnitude of the best b vectors was projected onto a time series (−110 to 0 ms in increments of 10 ms) of scalp maps. The spatial renderings of sensor contributions were produced by the topoplot function of EEGLAB, an open-source MATLAB toolbox for electrophysiological data processing (Delorme et al. (2004), supra, J. Neurosci. Methods, 134:9-21; http://sccn.ucsd.edu/eeglab), which performs biharmonic spline interpolation of the sensor values before plotting them (Sandwell 1987). To examine which time lags were the most important for decoding, for each scalp map the percentage of reconstruction contribution was determined as follows:

$$\% T_i = 100\% \times \frac{\sum_{n=1}^{N} \sqrt{b_{nix}^2 + b_{niy}^2 + b_{niz}^2}}{\sum_{n=1}^{N} \sum_{k=0}^{L} \sqrt{b_{nkx}^2 + b_{nky}^2 + b_{nkz}^2}}$$

for all i from 0 to L, where $\% T_i$ is the percentage of reconstruction contribution for a scalp map at time lag i.

Source Estimation with sLORETA

To better estimate the sources of cursor velocity encoding, standardized low-resolution brain electromagnetic tomography (sLORETA) software version 20081104 was utilized (Pascual-Marqui (2002) "*Standardized low-resolution brain electromagnetic tomography (sLORETA): technical details,*" Methods Find Exp. Clin. Pharmacol., 24 (Suppl D): 5-12; http://www.uzh.ch/keyinst/loreta.htm). Preprocessed (low-pass filtered and differenced) EEG signals from 34 channels for each subject were fed to sLORETA to estimate current sources. First, r values were computed between the squared time series of each of the 34 sensors with the 6239 time series from the sLORETA solution and then averaged across subjects. Second, the mean of the r values multiplied by the regression weights b of their associated sensors were assigned to each voxel. The regression weights had been pulled from the regression solution at the time lag with maximum $\% T_j$, which had the highest percentage of reconstruction contribution. Third, for visualization purposes, the upper quartile of voxels (r values weighted by b) was set to the value one, and the rest of the r values were set to zero. Finally, the binary-thresholded r values were plotted onto a surface model of the brain.

Eye and Muscle Activity Analysis

To assess the contribution of eye activity to decoding, the decoding procedure was executed off-line with channels of vertical and horizontal EOG activity included with the 34 channels of EEG activity. The percent contribution of these eye channels was then assessed by dividing the absolute value of their regression weights by the sum of the absolute value of all the regression weights. To assess whether muscle activity inadvertently aided cursor control, EMG signals from flexor and extensor muscles of the right forearm were cross correlated with the x and y components of cursor velocity over 200 positive and negative lags (−2 s to 2 s in increments of 10 ms). The start of the EMG and EEG/EOG recordings were not synchronized by computer, which is why the cross-correlation of the EMG and EOG signals at different lags was examined as opposed to only the zero-lag correlation. Prior to the cross correlation, the EMG signals were decimated 20 times after applying a 40 Hz low-pass antialiasing filter, rectified by taking the absolute value, low-pass filtered with a fourth-order, low-pass Butterworth filter at 1 Hz, and first-order differenced.

Results

Figure 3:
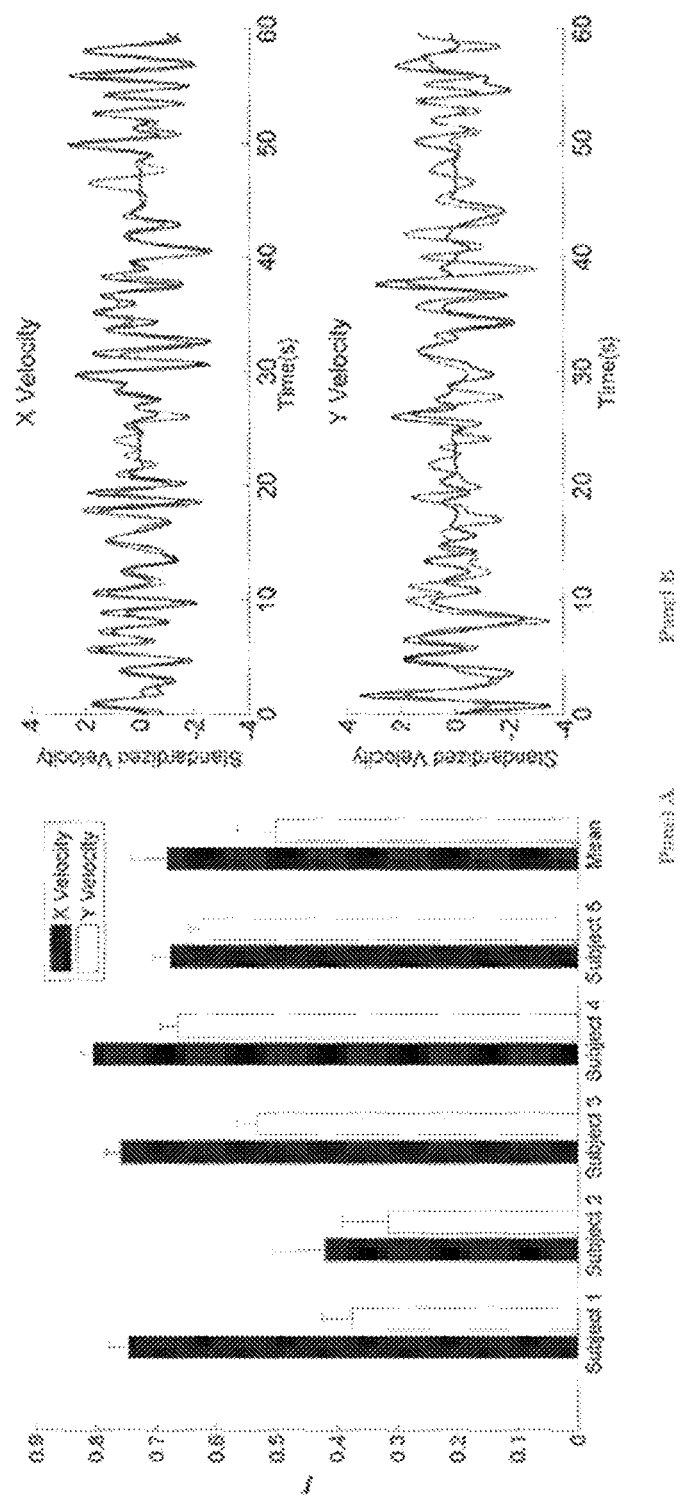
FIG. 3 depicts graphically EEG decoding accuracy of observed cursor velocity during the calibration phase according to the first embodiment. In Panel A, the mean±standard error (SE) of the decoding accuracies (r values) across cross-validation folds (n=10) for each subject was computed for x (black) and y (white) cursor velocities. As shown in Panel B, superimposed reconstructed velocity profiles (red) and actual velocity profiles (black) matched well (data from subject 1).

The accuracy of each subject's calibrated decoder was quantified by computing the mean of Pearson's r between actual and reconstructed cursor velocities across cross-validation folds. The EEG decoding accuracy of observed cursor velocity during the calibration phase is depicted graphically in FIG. 3. The mean±standard error (SE) of the decoding accuracies (r values) was computed across cross-validation folds (n=10) for each subject for x (black) and y (white) cursor velocities. Across subjects, the decoding accuracies for x and y velocities were correlated (r=0.67) even though the decoding accuracy for x velocity was consistently higher than that for y velocity. The across-subject mean r values for x and y velocities were 0.68 and 0.50 respectively, indicating high decoding accuracy for observed cursor movement.

Figure 4:
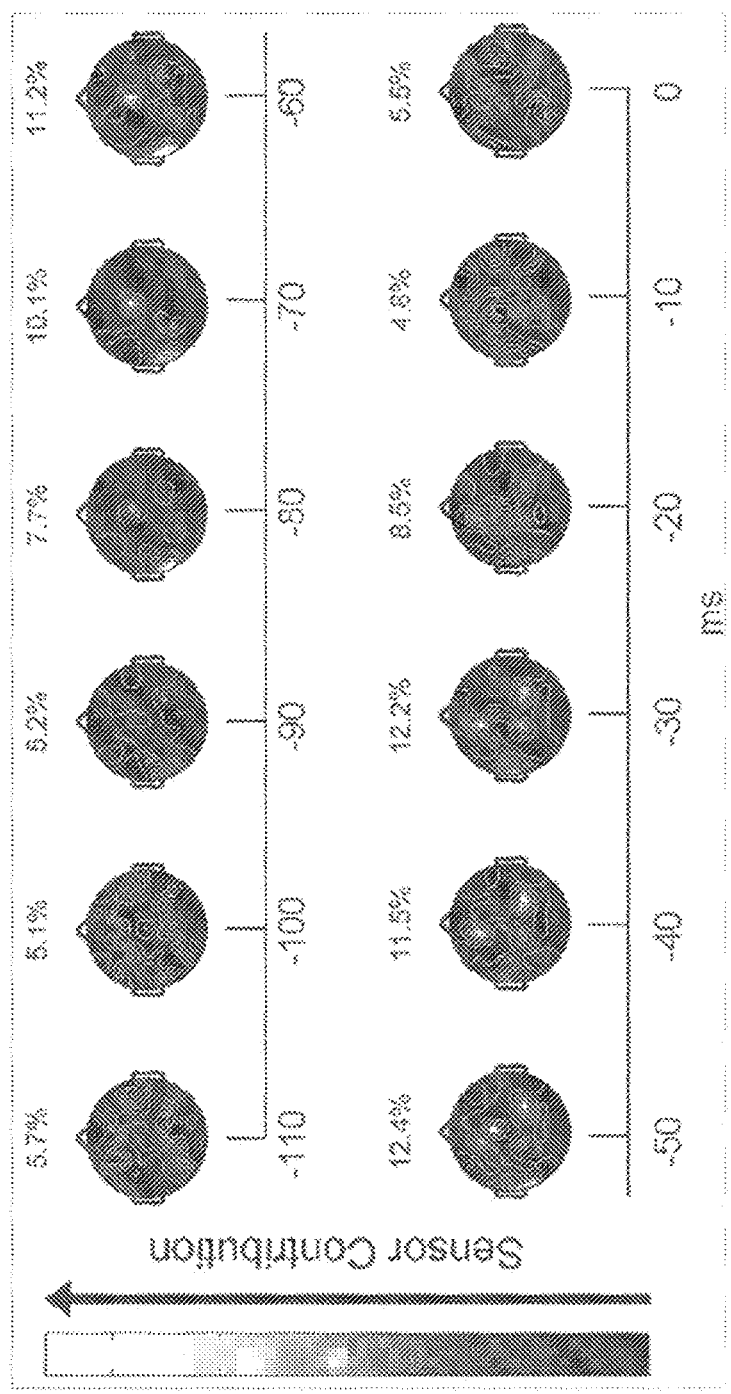
FIG. 4 illustrates scalp maps showing sensor contributions to the reconstruction of observed cursor velocity during the calibration phase of the first embodiment. Mean (n=5) scalp maps of the sensors revealed a network of frontal, central, and parietal involvement. In particular, F1, FCZ, and CP1-CP4 made the largest contribution. Light and dark colors represent high and low contributors, respectively. Each scalp map with its percentage contribution is displayed above its associated 10 ms time lag, revealing the 12.4% maximal contribution of EEG data at 50 ms in the past.

Scalp sensor contributions to the reconstruction of observed cursor velocity during the calibration phase are illustrated in FIG. 4. Light and dark colors represent high and low contributors, respectively. Mean (n=5) scalp maps of the sensor contributions revealed a network of frontal, central, and parietal involvement. Within this network, sensors over the frontocentral (F1, FCZ) and primary sensorimotor cortices (CP1-CP4) made the greatest contribution. Each scalp map with its percentage contribution is depicted above its associated 10 ms time lag, revealing a 12.4% maximal contribution of EEG data at 50 ms in the past.

Figure 5:
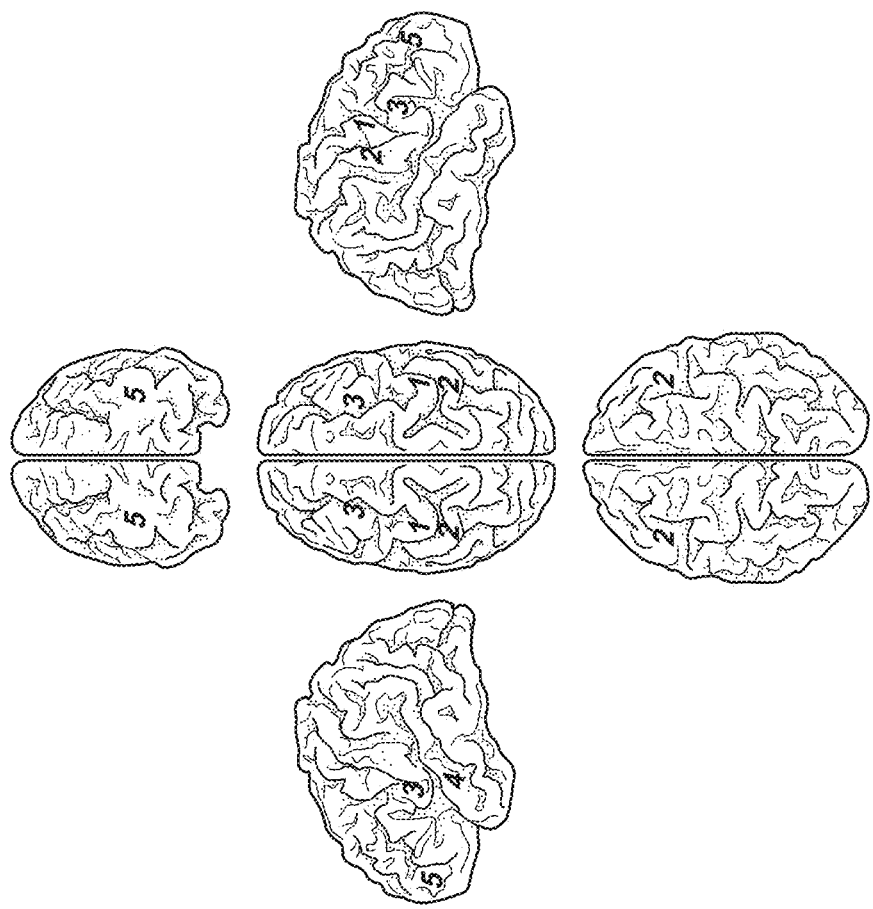
FIG. 5 illustrates sources that maximally encoded observed cursor velocity during the calibration phase of the first embodiment. Localized sources (yellow) from 50 ms in the past were overlaid onto a model of the brain in different orientations to reveal the involvement of the PrG (1), PoG (2), LPM (3), STS (4), and dorsal and ventral LPC (5).

Sources that maximally encoded observed cursor velocity during the calibration phase are illustrated in FIG. 5. Localized sources (shown as darker shaded portions) from 50 ms in the past were overlaid onto a model of the brain in different orientations to reveal the involvement of the PrG (1), PoG (2), LPM (3), STS (4), and dorsal and ventral LPC (5). In source space at 50 ms in the past, the precentral gyrus (PrG), postcentral gyrus (PoG), lateral premotor (LPM) cortex, superior temporal sulcus (STS), and dorsal and ventral portions of lateral prefrontal cortex (LPC) played a relatively large role in the encoding of observed cursor velocity.

Figure 6:
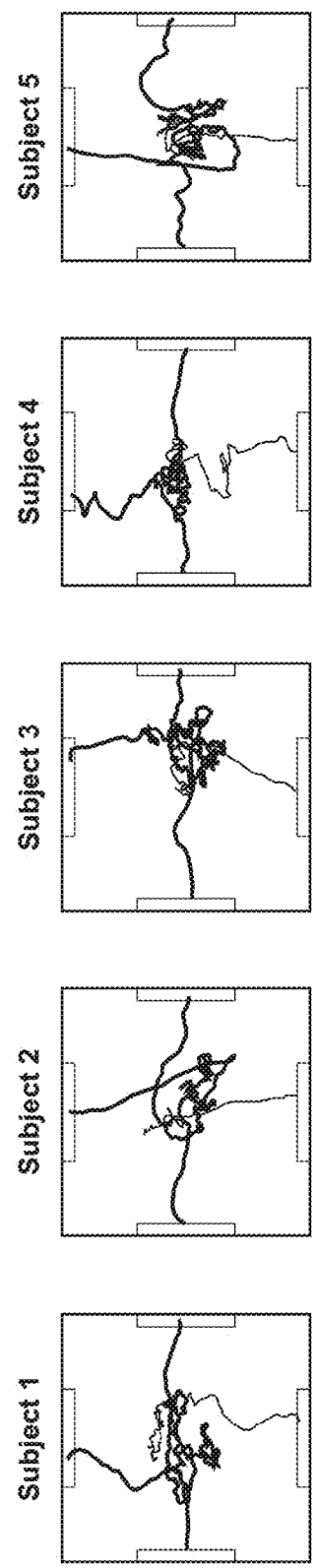
FIG. 6 illustrates mean brain-controlled cursor paths. Each path is the mean of the length-normalized trials for a single direction (left, top, right, or bottom) across all trials of all runs for a subject. Trials in which subjects did not acquire the target within 15 s were excluded from the analysis.

During the target acquisition phase, the subjects controlled the cursor with their EEG signals to hit targets that appeared one at a time pseudorandomly at the left, top, right, or bottom of the workspace. Four 10 min runs of target acquisition were performed with a rest interval of 1 min between runs. The length-normalized cursor paths confirmed the subjects' ability to move from the center to the target. Mean brain-controlled cursor paths are illustrated in FIG. 6. Each path is the mean of the length-normalized trials for a single direction (left, top, right, or bottom) across all trials of all runs for a subject. Trials in which subjects did not acquire the target within the 15 second time limit were not included in the analysis. For each target of each subject, the target hit rate and movement time (MT) across runs are presented in Table 1 below. The overall means±SE of the hit rate and MT were 73±4% and 8.18±0.1 8 seconds.

TABLE 1

Mean (SE) of Target Hit Rate and MT for each target of each subject across runs (n = 4)

|  | Left | | Top | | Right | | Bottom | | Mean | |
| --- | --- | --- | --- | --- | --- | --- | --- | --- | --- | --- |
|  | Hit % | MT | Hit % | MT | Hit % | MT | Hit % | MT | Hit % | MT |
| Subject 1 | 94 | 7.30 | 66 | 8.80 | 98 | 7.43 | 55 | 10.7 | 78 | 8.56 |
|  | (2) | (0.60) | (8) | (0.57) | (2) | (0.49) | (9) | (0.68) | (11) | (0.80) |
| Subject 2 | 83 | 8.97 | 96 | 7.70 | 85 | 7.68 | 85 | 7.12 | 87 | 7.87 |
|  | (5) | (0.49) | (4) | (0.49) | (2) | (0.55) | (4) | (0.40) | (3) | (0.39) |

TABLE 1-continued

Mean (SE) of Target Hit Rate and MT for each target of each subject across runs (n = 4)

| | Left | | Top | | Right | | Bottom | | Mean | |
|---|---|---|---|---|---|---|---|---|---|---|
| | Hit % | MT | Hit % | MT | Hit % | MT | Hit % | MT | Hit % | MT |
| Subject 3 | 84 | 7.51 | 45 | 11.8 | 100 | 5.50 | 67 | 8.89 | 74 | 8.44 |
| | (9) | (0.53) | (4) | (0.93) | (0) | (0.37) | (9) | (0.58) | (12) | (1.33) |
| Subject 4 | 71 | 6.86 | 33 | 9.49 | 65 | 9.87 | 21 | 8.59 | 47 | 8.70 |
| | (7) | (0.67) | (7) | (1.42) | (6) | (0.79) | (4) | (1.39) | (12) | (0.67) |
| Subject 5 | 57 | 10.0 | 100 | 5.58 | 60 | 9.06 | 100 | 4.59 | 79 | 7.32 |
| | (14) | (0.69) | (0) | (0.26) | (18) | (0.70) | (0) | (0.18) | (12) | (1.32) |
| Mean | 78 | 8.13 | 68 | 8.69 | 81 | 7.91 | 65 | 7.98 | 73 | 8.18 |
| | (6) | (0.60) | (13) | (1.03) | (8) | (0.75) | (14) | (1.02) | (4) | (0.18) |

Figure 7:
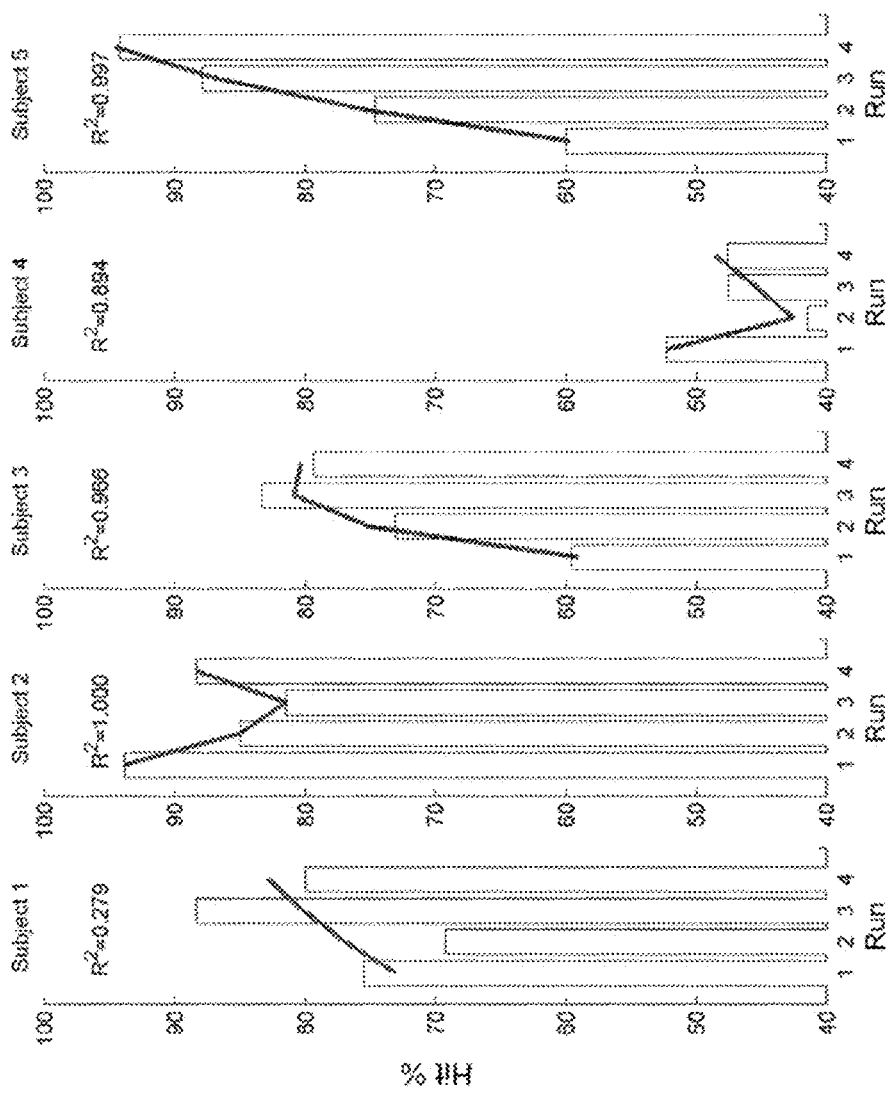
FIG. 7 illustrates graphically changes in target hit rate across runs in the first embodiment. Each bar represents the target hit rate across targets. A double exponential curve was fitted to the target hit rates across runs for each subject (red). The coefficient of determination ($R^2$) of the fit is displayed within each subplot.

To examine whether subjects adapted across runs of the target acquisition phase, the target hit rate for all targets taken together was fitted across runs with a double exponential curve for each subject. Changes in target hit rate across runs is depicted graphically in FIG. 7. Each bar represents the target hit rate across targets. A double exponential curve was fitted to the target hit rates across runs for each subject (depicted as a line extending across an upper end of the bars for each subject). The coefficient of determination ($R^2$) of the fit is displayed within each subplot. Subjects 3 and 5 most clearly demonstrated positive adaptation across runs. The hit rate of subjects 2 and 4 worsened initially and then began to improve.

To visualize the contributions of scalp regions and current sources to the reconstruction of cursor velocity, the weights of the decoder were projected onto scalp maps, and sLORETA (Pascual-Marqui (2002), supra, Methods Find Exp. Clin. Pharmacol., 24 (Suppl D): 5-12) was employed. Scalp maps of sensor contributions to the reconstruction of observed cursor movements in the calibration phase depicted the contributions as a network of frontal, central and parietal regions. Within this network, sensors over the frontocentral and primary sensorimotor cortices made the greatest contribution. Concerning time lags, EEG data from 50 ms in the past supplied the most information. In source space at 50 ms in the past, the precentral gyrus (PrG), postcentral gyrus (PoG), lateral premotor (LPM) cortex, superior temporal sulcus (STS), and dorsal and ventral portions of lateral prefrontal cortex (LPC) played a large role in the encoding of observed cursor velocity.

Figure 8:
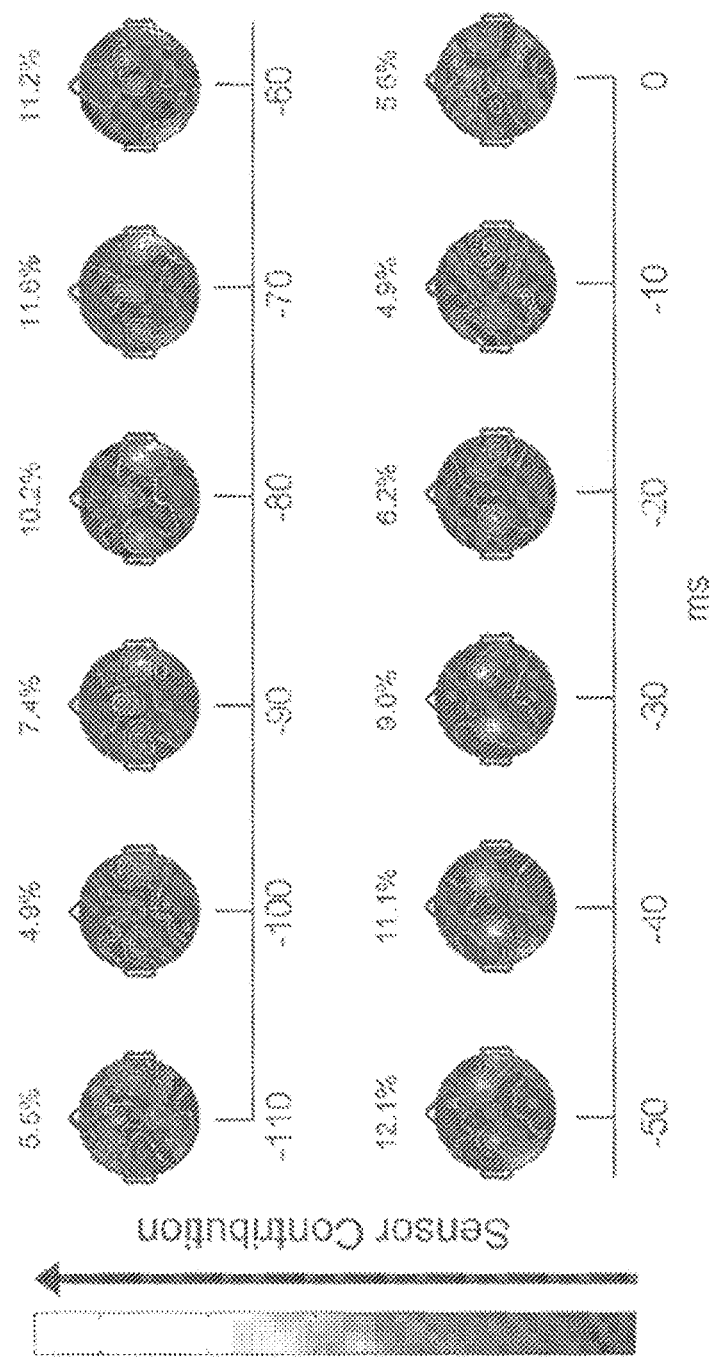
FIG. 8 illustrates scalp maps showing sensor contributions to the brain-controlled cursor velocity during the target acquisition phase of the first embodiment. Mean (n=5) scalp maps of the sensors weights from the subjects' best runs revealed a network that had shifted to involve more central regions than the network of the calibration phase. Light and dark colors represent high and low contributors, respectively. Each scalp map with its percentage contribution is displayed above its associated 10 ms time lag, revealing the 12.1% maximal contribution of EEG data at 50 ms in the past.

Scalp maps of sensor contributions to the brain-controlled cursor velocity were generated from the mean of each subject's best run in the target acquisition phase. They depicted the contributions as having shifted to be more focused within central regions. Scalp sensor contributions to the brain-controlled cursor velocity during the target acquisition phase are depicted in FIG. 8. Light and dark colors represent high and low contributors, respectively. Mean (n=5) scalp maps of the sensors weights from the subjects' best runs revealed a network that had shifted to involve more central regions than the network of the calibration phase. Each scalp map with its percentage contribution is displayed above its associated 10 ms time lag, revealing the 12.1% maximal contribution of EEG data at 50 ms in the past.

As in the calibration phase, EEG data from 50 ms in the past supplied the most information with 12.1% of the total contribution. In source space at 50 ms in the past, compared to the calibration phase, a large shift occurred from anterior (fronto-central) to posterior (centro-posterior) neural regions. More specifically, there was much less involvement of the LPC, the PrG and PoG exhibited an even more widespread involvement, and the inferior parietal lobule (IPL) made a large contribution.

Figure 9:
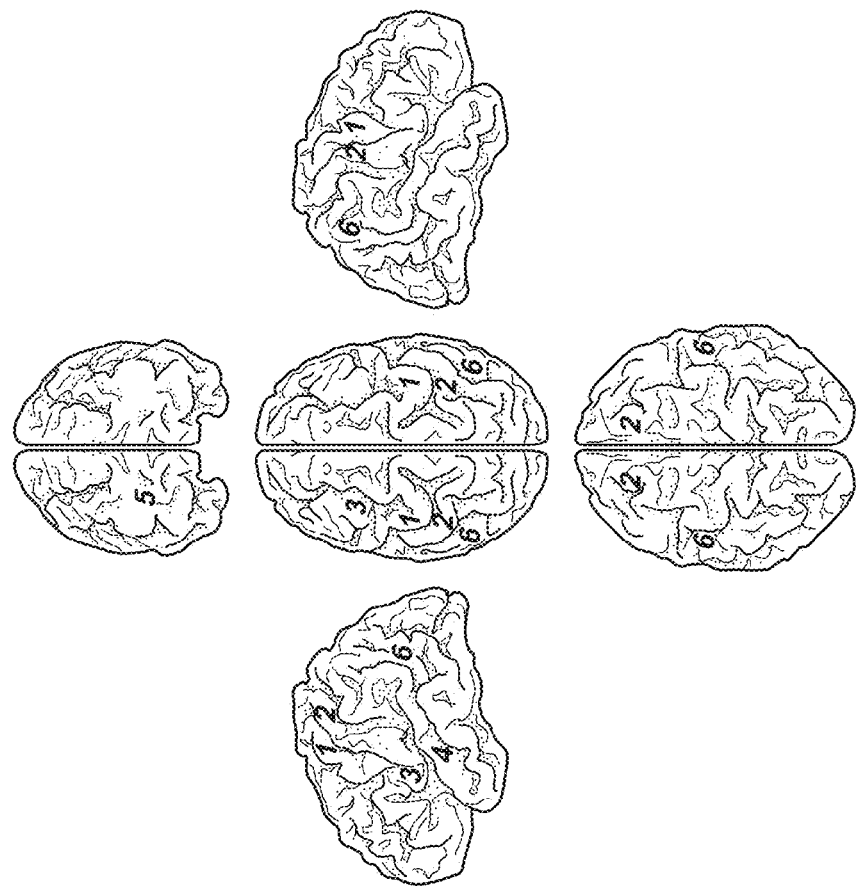
FIG. 9 illustrates sources that maximally encoded brain-controlled cursor velocity during the target acquisition phase of the first embodiment. Localized sources (yellow) from 50 ms in the past were overlaid onto a model of the brain in different orientations to reveal a substantial involvement of PrG (1) and PoG (2) and some involvement of LPM (3). As in the calibration phase, the STS (4) was involved. In contrast to the calibration phase, the LPC (5) played a minor role, and the IPL (6) played a major role.

Sources that maximally encoded brain-controlled cursor velocity during the target acquisition phase are illustrated in FIG. 9. Localized sources (shown as darker shaded portions) from 50 ms in the past were overlaid onto a model of the brain in different orientations to reveal a substantial involvement of PrG (1) and PoG (2) and some involvement of LPM (3). As in the calibration phase, the STS (4) was involved. In contrast to the calibration phase, the LPC (5) played a minor role, and the IPL (6) played a relatively major role.

Eyes and Muscle Contributions

A concern in BCI studies is that eye or muscle movements may contaminate EEG signals, thereby inadvertently aiding the control of a device and/or environment that should be controlled by thought-generated neural signals alone. To address this concern, we executed the off-line decoding procedure with channels of vertical and horizontal EOG activity included, and assessed the percent contribution of these eye channels:

TABLE 2

Percent Contribution of EOG Activity to Cursor Velocity Reconstruction

| | Calibration | | Target acquisition (best run) | |
|---|---|---|---|---|
| | X | Y | X | Y |
| Subject 1 | 0.30 | 1.58 | 0.00 | 0.01 |
| Subject 2 | 0.00 | 0.01 | 0.20 | 0.18 |
| Subject 3 | 1.99 | 9.60 | 1.54 | 0.47 |
| Subject 4 | 0.00 | 0.01 | 94.9 | 0.04 |
| Subject 5 | 0.34 | 0.65 | 0.06 | 0.03 |

The percent contributions were low for the calibration and target acquisition phases except for a high percent contribution (94.9%) to x velocity reconstruction for Subject 4 during target acquisition. Interestingly, subject 4 had the lowest decoding accuracy of all participants, suggesting that eye movements disrupted decoding. Furthermore, the fact that hardly any extreme frontal contribution is observed in the scalp maps and sLORETA plots is a testament to the non-contribution of EOG activity to decoding.

To assess whether muscle activity aided cursor control, EMG signals from flexor and extensor muscles of the right forearm were cross correlated with the x and y components of cursor velocity to find that all correlations were relatively low:

TABLE 3

Mean (SD) of Maximum Absolute r Values from Cross
Correlation of Forearm Flexor and Extensor EMG
Activity with x and y Components of Cursor Velocity

|  | Calibration | | Target acquisition (best run) | |
| --- | --- | --- | --- | --- |
|  | X | Y | X | Y |
| Flexor | 0.05 | 0.05 | 0.04 | 0.07 |
|  | (0.04) | (0.04) | (0.02) | (0.03) |
| Extensor | 0.03 | 0.04 | 0.07 | 0.05 |
|  | (0.02) | (0.01) | (0.08) | (0.04) |

Discussion

The training by cursor observation in the decoder calibration phase may have engaged the putative human MNS, which predicts and interprets one's own actions and the actions of others (Tkach et al. (2008), supra, Curr. Opin. Neurobiol., 18:589-594). In fact, neuronal activity acquired from intracortical microelectrode arrays implanted in the dorsal premotor cortex (PMd) and the arm area of the PrG (primary motor cortex, M1), common sites for BCI-related studies, exhibits qualities of mirror neurons during observation of cursor movements (Cisek et al. (2004) "*Neural correlates of mental rehearsal in dorsal premotor cortex*," Nature, 431:993-996; Wahnoun et al (2006) "*Selection and parameterization of cortical neurons for neuroprosthetic control*," J. Neural Eng., 3:162-171; Tkach et al. (2007), supra, J. Neurosci. 27:13241-13250).

Current electrophysiological correlates of the putative human MNS, as acquired through EEG, are based on modulation of the mu rhythm (8-13 Hz), which exhibits suppression during action observation and action performance (Perry et al. (2009) "*Mirror activity in the human brain while observing hand movements: a comparison between EEG desynchronization in the mu-range and previous fMRI results*," Brain Res., 1282:126-132). These EEG correlates at the scalp level with high temporal resolution have been reported to be similar to those revealed by neural hemodynamics with high spatial resolution acquired with functional magnetic imaging (fMRI). Since our examination of cortical sources that encoded observed cursor velocity revealed some regions commonly held to comprise the canonical human MNS (ventral LPM, STS, and LPC) (Iacoboni et al. (2006) "*The mirror neuron system and the consequences of its dysfunction*," Nat. Rev. Neurosci., 7:942-951) and regions reportedly containing mirror neurons related to the task (PMd, M1) (Cisek et al. (2004), supra, Nature, 431:993-996; Wahnoun et al (2006), supra, J. Neural Eng., 3:162-171; Tkach et al. (2007), supra, J. Neurosci. 27:13241-13250), our method appears to provide detailed temporal and spatial information about the internal representations of both observed and executed actions, which is not provided by the study of mu rhythm dynamics or hemodynamics alone. Our method provides further spatiotemporal evidence that the MNS is involved during observed cursor movement by indicating the presence of planning activity that peaks at 50 ms in the past, excluding the decoding of passive viewing as an explanation and suggesting predictive decoding informed by forward models (Miall (2003) "*Connecting mirror neurons and forward models*," NeuroReport, 14:2135-2137).

Comparison to Other BCI Methods

Current electrophysiological correlates of the putative human MNS, as acquired through EEG, are based on modulation of the mu rhythm (8-13 Hz), which exhibits suppression during action observation and action performance (Perry et al. (2009), supra, Brain Res., 1282:126-132). These EEG correlates at the scalp level have been reported to be similar to those revealed by neural hemodynamics acquired with functional magnetic imaging (fMRI). However, for examining, in spatial detail, the widespread networks of cortical regions that may compose the human MNS, arguably fMRI is considered by many to be the optimal tool. The present examination of cortical sources that encoded observed cursor velocity revealed some regions commonly held to comprise the canonical human MNS (ventral LPM, STS, and LPC (Iacoboni et al. (2006), supra, Nat. Rev. Neurosci., 7:942-951) and regions reportedly containing mirror neurons related to the task (PMd, M1) (Cisek et al. (2004), supra, Nature, 431:993-996; Wahnoun et al (2006), supra, J. Neural Eng., 3:162-171; Tkach et al. (2007), supra, J. Neurosci. 27:13241-13250). The disclosed method provides detailed temporal and spatial temporal information about the internal representations of both observed and executed actions, which is not provided by the study of mu rhythm dynamics or hemodynamics alone.

Therefore, the disclosed method is particularly suitable for investigation into the development and plasticity of the hypothesized MNS in humans. Interestingly, that our subjects' mean decoding accuracy was double that of studies that acquired neural signals with intracranial microelectrode arrays (Kim et al (2008), supra, J. Neural Eng., 5:455-476; Truccolo et al. (2008), supra, J. Neurosci., 28:1163-1178) could be attributed to capturing more information for reconstruction by recording neural signals from an MNS network instead of only mirror neurons in M1. The disclosed method also provides further evidence that the MNS is involved during observed cursor movement by indicating the presence of planning activity that peaks at 50 ms in the past, excluding the decoding of passive viewing as an explanation and suggesting predictive decoding informed by forward models (Miall (2003), supra, NeuroReport, 14:2136-2137).

The off-line decoding results of the calibration phase that used observation of biologically plausible cursor movement were higher than those of invasive BCI studies, implying the involvement of a widespread mirror neuron system (MNS) in humans. In the on-line target acquisition phase of the disclosed system, subjects effectively controlled a cursor with their EEG signals alone with accuracies comparable to other noninvasive and invasive BCI studies aimed at two dimensional cursor control (but with such comparable studies requiring extension and lengthy training by the users).

The disclosed noninvasive EEG-based BCI study employs continuous decoding of imagined natural movement. In contrast, previous work in EEG-based BCI systems for cursor control required subjects to overcome an initial disconnect between intended movement and neural activity in order to learn how to modulate their sensorimotor rhythms to control the cursor. These studies based on sensorimotor rhythms required weeks to months of training before levels of performance were deemed sufficient for reporting (Wolpaw et al. (2004), supra, Proc. Natl. Acad. Sci. USA, 101:17849-17854). We believe the fact that we used a decoder based on imagined/observed natural movement, as opposed to neuro-feedback training of sensorimotor rhythms, reduced the subject training requirements of our target acquisition phase to only a single brief practice session (~20 minutes). An ECoG study based on sensorimotor rhythms that had objectives similar to ours also observed that several subjects learned to control a 2D cursor over a short period of time (Schalk et al. (2008), supra, J. Neural Eng., 5:75-84). Although this ECoG study reduced training time compared to previous EEG studies (Wolpaw et al. (2004), supra, Proc. Natl. Acad. Sci. USA, 101:17849-17854), some drawbacks included that pre-training time was still taken for the initial selection of control features and for training subjects to first move the cursor in one dimension at a time. We were able to bypass these two pre-training steps. Another drawback of the ECoG study was that all five subjects used overt movement for initial selection of features, and two subjects used overt movement throughout the study.

Additionally, the results of our target acquisition phase compare favorably to those in tetraplegic humans that were implanted with intracortical arrays in the arm area of M1 (Hochberg et al (2006), supra, Nature, 442:164-171; Kim et at (2008), supra, J. Neural Eng., 5:455-476) even though the performance results of those studies were only computed on data collected weeks to months after training began. A comparison of the aforementioned studies to the present invention is provided:

TABLE 4

Comparison to Prior Human BCI Studies of Two Dimensional Cursor Control

| | Number of subjects | Neural data | Target size as % of workspace | Timeout (s) | Movement time (s) | Target hit % |
|---|---|---|---|---|---|---|
| Wolpaw et al. (2004) | 4 | EEG | 4.9 | 10 | 1.9 | 92 |
| Hochberg et al. (2006) | 1 | single units | NA | 7 | 2.5 | 85 |
| Kim et al. (2008) | 2 | single units | 1.7 | 7 | 3.1 | 75 |
| Schalk et al. (2008) | 5 | ECoG | 7 | 16.8 | 2.4 | 63 |
| Present study | 5 | EEG | 1.3 | 15 | 8.2 | 73 |

Prior EEG-based BCI systems for cursor control required subjects to learn to modulate sensorimotor rhythms to move the cursor akin to neuro/biofeedback training. Such studies based on sensorimotor rhythms required weeks to months of training before levels of performance were deemed sufficient for reporting (Wolpaw et al. (2004), supra, Proc. Natl. Acad. Sci. USA, 101:17849-17854).

The disclosed noninvasive BCI system utilizes a decoder based on imagined/observed natural movement, which substantially reduces the training requirements for a user to only a single relatively brief practice session (~20 minutes). Thus, the results achieved in the present system present a significant advancement over prior systems and studies. The results from the target acquisition phase of the present invention compare favorably to those in tetraplegic humans that were implanted with intracortical arrays in the arm area of M1 (Hochberg et al (2006), supra, Nature, 442:164-171; Kim et al (2008), supra, J. Neural Eng., 5:455-476), even though the performance results of those studies were only computed on data collected weeks to months after training began.

Besides differences in training time, the disclosed system differs from prior studies in its reporting of cortical sources involved in encoding cursor control. One notable difference between the regions that encoded for observed cursor velocity and brain-controlled cursor velocity were with the PrG, PoG, IPL, and LPC. There was a more widespread contribution from the PrG, PoG, and IPL during brain control, which could simply reflect the increased involvement of imagined motor execution (Miller et al. (2010) "Cortical activity during motor execution, motor imagery, and imagery-based online feedback," Proc. Natl. Acad. Sci. USA, 107:4430-4435) especially since these regions have previously been shown to be engaged in encoding cursor kinematics (Jerbi et al. (2007), supra, Proc. Natl. Acad. Sci. USA, 104:7676-7681; Bradberry et al. (2009a), supra, Neuro-image, 47:1691-1700). The contribution from the LPC was largely attenuated during brain-controlled cursor movements, suggesting a transition out of the imitative learning environment of cursor observation (Vogt et al. (2007) "Prefrontal involvement in imitation learning of hand actions: effects of practice and expertise," NeuroImage, 37:1371-1383).

The BCI system according to the first invention may be particularly beneficial for patients with substantially or completely impaired upper limb movement, wherein no overt movement by the subject is required. In other embodiments, some limb movement is utilized.

A noninvasive BCI system according to another embodiment decodes the kinematics of natural hand movements from EEG signals in combination with recorded hand and/or finger movement. An example experiment of an EEG-based BCI system according to the second embodiment is provided:

EXAMPLE 2

Methods and Materials

Figure 10:
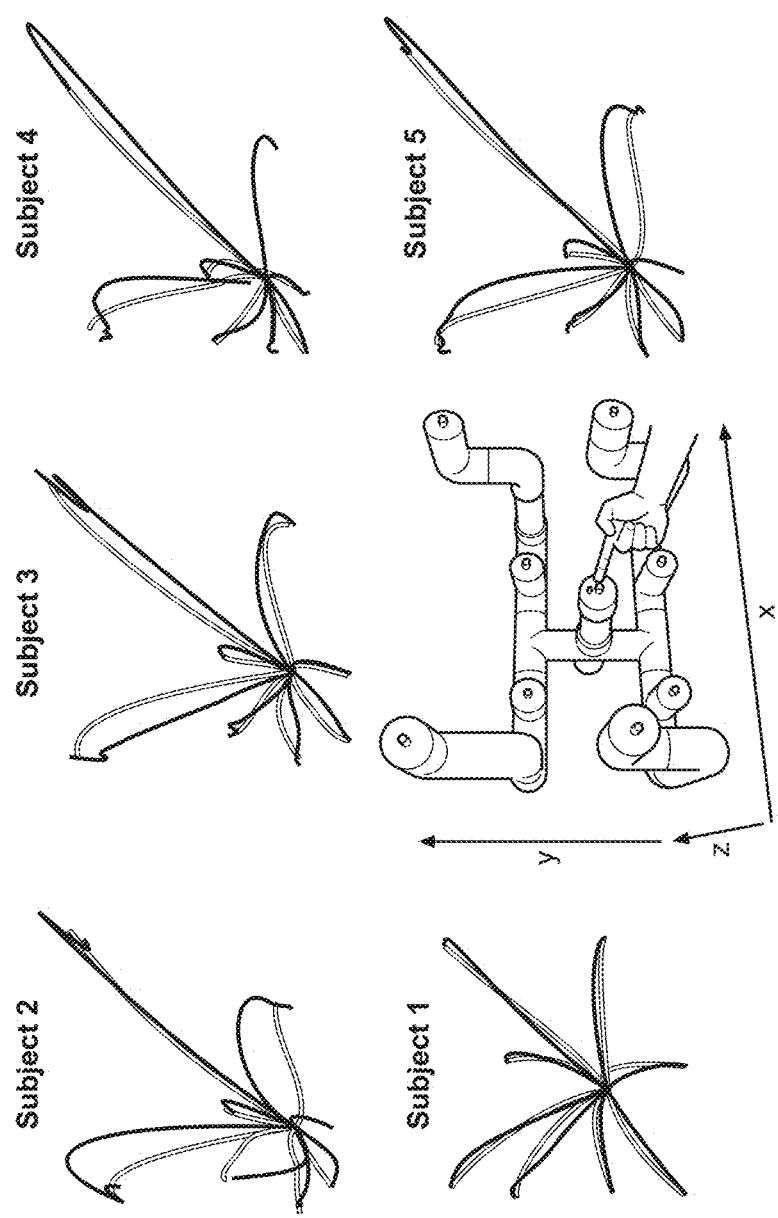
FIG. 10 illustrates a setup of an EEG-based BCI system according to a second embodiment, and also illustrates finger paths for five subjects. The reaching apparatus is shown in the middle along with the Cartesian coordinate system used. The distance from the center position to each of the targets was about 22 cm. Mean finger paths for center-to-target (black) and target-to-center (gray) movements exhibited movement variability among subjects.

Referring to FIG. 10, five healthy, right-handed subjects sat upright in a chair and executed self-initiated, center-out reaches to self selected push-button targets near eye level. The subjects were instructed to attempt to make uniformly distributed random selections of the eight targets without counting. Subjects were further instructed to fixate on an LED on the center target throughout data collection and to only blink when their hand was resting at the center target. To ensure the minimization of eye movements, a researcher monitored the subjects' eyes during data collection, and the correlation between electrooccular activity and hand kinematics was analyzed off-line (available at www.jneurosci.org as supplemental material). For each subject, the experiment concluded after each target was acquired at least 10 times.

A 64-sensor cap for sensing EEG signals (e.g., such as available from Electro-Cap International Inc. of Eaton, Ohio) was placed on the head of each subject and in accordance with the extended International 10-20 system with ear-linked reference. The cap was used to collect 58 channels of EEG activity from each subject.

Continuous EEG signals were sampled at 1000 Hz, bandpass filtered from 0.5 to 100 Hz, and notch filtered at 60 Hz. Horizontal and vertical electrooccular activity was measured with bipolar sensor montages. Hand position was sampled at 100 Hz using a motion-sensing system that tracked an infrared LED secured to the fingertip. The EEG data were decimated from 1 kHz to 100 Hz by applying a low-pass, antialiasing filter with a cutoff frequency of 40 Hz and then down sampling by a factor of 10. A zero phase, fourth-order, low-pass Butterworth filter with a cutoff frequency of 1 Hz was then applied to the kinematic and EEG data. Next, the temporal difference of the EEG data was computed. To examine relative sensor contributions in the scalp map analysis described in a section below, data from each EEG sensor were standardized as follows:

$$S_n[t] = \frac{v_n[t] - \mu_{v_n}}{\sigma_{v_n}},$$

for all n from 1 to N, where $S_n[t]$ and $v_n[t]$ are, respectively, the standardized and differenced voltage at sensor n at time t, $\mu_{v_n}$, and $\sigma_{v_n}$ are, respectively, the mean and SD of $v_n$, and N is the number of sensors.

To continuously decode hand velocity from the EEG signals, the following linear decoding was utilized:

$$x[t] - x[t-1] = a_x + \sum_{n=1}^{N} \sum_{k=0}^{L} b_{nkx} S_n[t-k], \quad (2)$$

$$y[t] - y[t-1] = a_y + \sum_{n=1}^{N} \sum_{k=0}^{L} b_{nky} S_n[t-k], \quad (3)$$

$$z[t] - z[t-1] = a_z + \sum_{n=1}^{N} \sum_{k=0}^{L} b_{nkz} S_n[t-k], \quad (4)$$

where $x[t]-x[t-1]$, $y[t]-y[t-1]$, and $z[t]-z[t-1]$ are, respectively, the horizontal, vertical, and depth velocities of the hand at time sample t, N is the number of EEG sensors, L (=10) is the number of time lags, Sn [t-k] is the standardized difference in voltage measured at EEG sensor n at time lag k, and the a and b variables are weights obtained through multiple linear regression. The three most frontal sensors were excluded from the analysis to further mitigate the influence of any eye movements on reconstruction, resulting in an N of 55 sensors.

For each subject, the collected continuous data contained about 80 trials. All continuous data were used in an 8×8-fold cross-validation procedure to assess the decoding accuracy. The cross-validation procedure was considered complete when all of the eight combinations of training and testing data were exhausted, and the mean Pearson correlation coefficient (r) between measured and reconstructed kinematics was computed across folds. Before computing r, the kinematic signals were smoothed with a zero-phase, fourth-order, low-pass Butterworth filter with a cutoff frequency of 1 Hz.

Sensor Sensitivity Curves

Curves depicting the relationship between decoding accuracy and the number of sensors used in the decoding method were plotted for the x, y, and z dimensions of hand velocity. First, for each subject, each of the 55 sensors was assigned a rank according to the following:

$$R_n = \frac{1}{L+1} \sum_{k=0}^{L} \sqrt{b_{nkx}^2 + b_{nky}^2 + b_{nkz}^2},$$

for all n from 1 to N, where Rn is the rank of sensor n, and the b variables are the best regression weights (Sanchez et al. (2004) "*Ascertaining the importance of neurons to develop better brain-machine interfaces*," IEEE Trans. Biomed. Eng., 51:943-953). Next, the decoding method with cross-validation as described above and ranking method were iteratively executed using backward elimination with a decrement step of three. The mean and SEM of r values computed across subjects were plotted against the number of sensors.

Scalp Maps of Sensor Contributions

To graphically assess the relative contributions of scalp regions to the reconstruction of hand velocity, the across-subject mean of the magnitude of the best b vectors was projected onto a time series (-100-0 ms in increments of 10 ms) of scalp maps. These spatial renderings of sensor contributions were produced by the topoplot function of EEGLAB (Delorme et al. (2004) "*EEGLAB: an open source toolbox for analysis of single-trial EEG dynamics including independent component analysis*," J. Neurosci. Methods, 134:9-21; http://sccn.ucsd.edu/eeglab). To examine which time lags were the most important for decoding, for each scalp map, the percentage of reconstruction contribution was defined as follows:

$$\% T_i = 100\% \times \frac{\sum_{n=1}^{N} \sqrt{b_{nix}^2 + b_{niy}^2 + b_{niz}^2}}{\sum_{n=1}^{N} \sum_{k=0}^{L} \sqrt{b_{nkx}^2 + b_{nky}^2 + b_{nkz}^2}},$$

for all i from 0 to L, where % Ti is the percentage of reconstruction contribution for a scalp map at time lag i.

Source Estimation with sLORETA

To better estimate the sources of hand-velocity encoding, we used sLORETA (Pascual-Marqui (2002), supra, Methods Find Exp. Clin. Pharmacol., 24 (Suppl D): 5-12; http://www.uzh.ch/keyinst/loreta.htm). Preprocessed EEG signals from all 55 channels for each subject were fed to sLORETA to estimate current sources. These EEG signals had been preprocessed in the same manner as that for decoding. First, r values were computed between the squared time series of each of the 55 sensors with the 6239 time series from the sLORETA solution and then averaged across subjects. Second, the maximum r value was assigned to each voxel after being multiplied by the regression weight b of its associated sensor. The regression weights had been pulled from the regression solution at time lag 60 ms, which had the highest percentage of reconstruction contribution. Third, for visualization purposes, the highest 5% of the voxels (r values weighted by b) were set to the value 1, and the rest of the r values were set to zero. Finally, these binary-thresholded r values were plotted onto axial slices of the brain from the Colin27 volume (Holmes et al., 1998). All reported coordinates of regions of interest are in MNI (Montreal Neurological Institute) space.

Movement Variability

For each subject, three measures of movement variability were computed: the coefficient of variation (CV) for movement time (MT), the CV for movement length (ML), and the kurtosis of movement. MT and ML were computed on a trial basis with a trial defined as the release of a push button to the press of a push button (center-to-target or target-to-center). The mean and SD of the measures were then computed, and the SD was divided by the mean to produce the CV. Kurtosis was defined as follows:

$$k = \frac{E(h - \mu_h)^4}{\sigma_h^4} - 3,$$

where k is the kurtosis, E( ) is the expected value operator, h is the hand velocity, and $\mu_h$ and $\sigma_h$ are, respectively, the mean and SD of the hand velocity. Single trials of velocity profiles for x, y, and z dimensions were re-sampled to normalize for length and then concatenated before computing kurtosis. The relationship between movement variability and decoding accuracy was examined by computing the r value between the quantities. The sample sizes were small (n=5) for decoding accuracy and each measure of movement variability, so 10,000 r values were bootstrapped for each comparison, and the median and confidence intervals of the resultant non-Gaussian distributions were calculated using the bias-corrected and accelerated percentile method (Efron et al. (1998) "An introduction to the bootstrap," Boca Raton, Fla.: CRC).

Results

Figure 11:
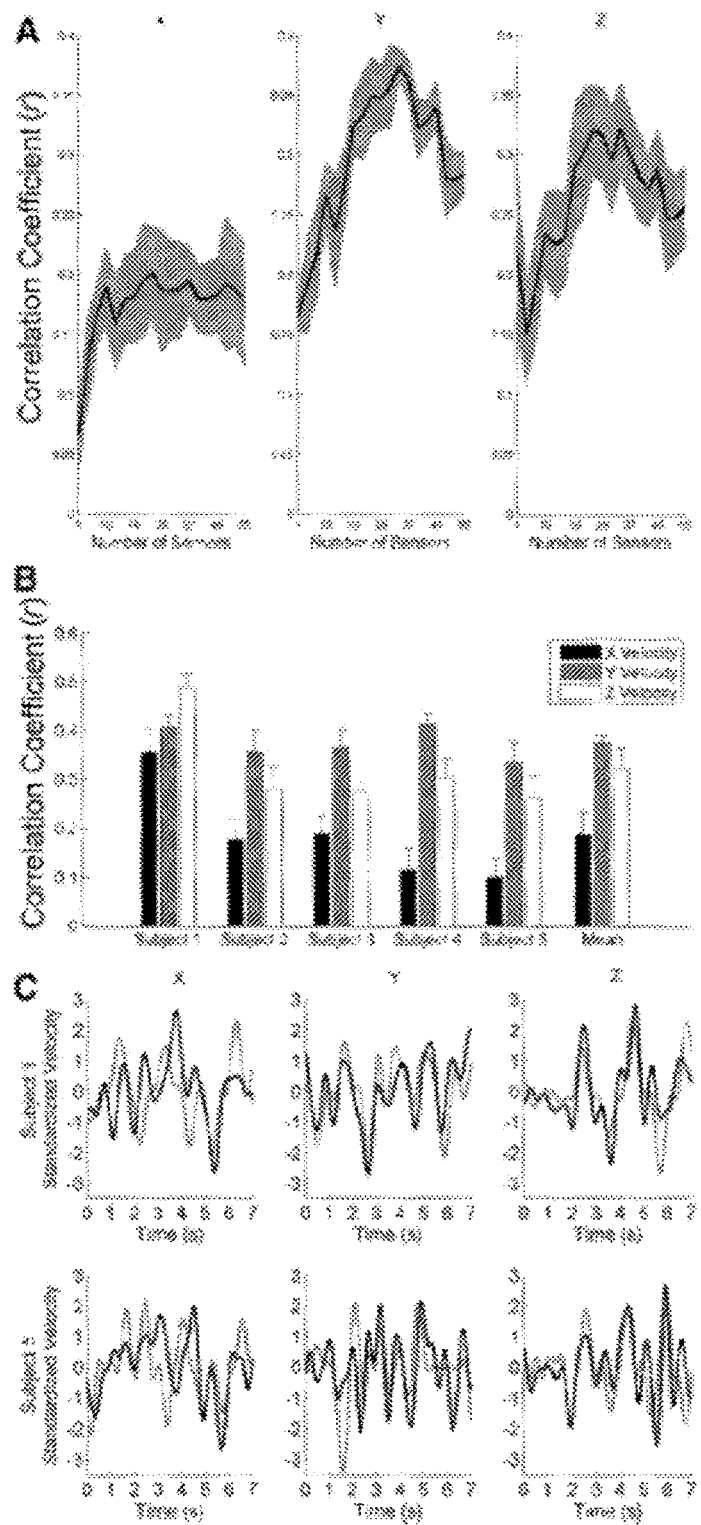
FIG. 11 illustrates graphically EEG decoding accuracy of hand velocity in the second embodiment. As shown in Panel A, the mean (black)±SEM (gray) of the r values across subjects (n=5) versus the number of sensors exhibited a peak at 34 sensors. In Panel B, with 34 sensors, the mean±SEM of the r values across cross-validation folds (n=8) for each subject for x (black), y (gray), and z (white) velocities was computed. Shown in Panel C, reconstructed (black) and measured (gray) velocity profiles demonstrated similarities. Exemplar velocity profiles from the subjects with the best (subject 1, top row) and the worst (subject 5, bottom row) decoding accuracies are shown.
Figure 23:
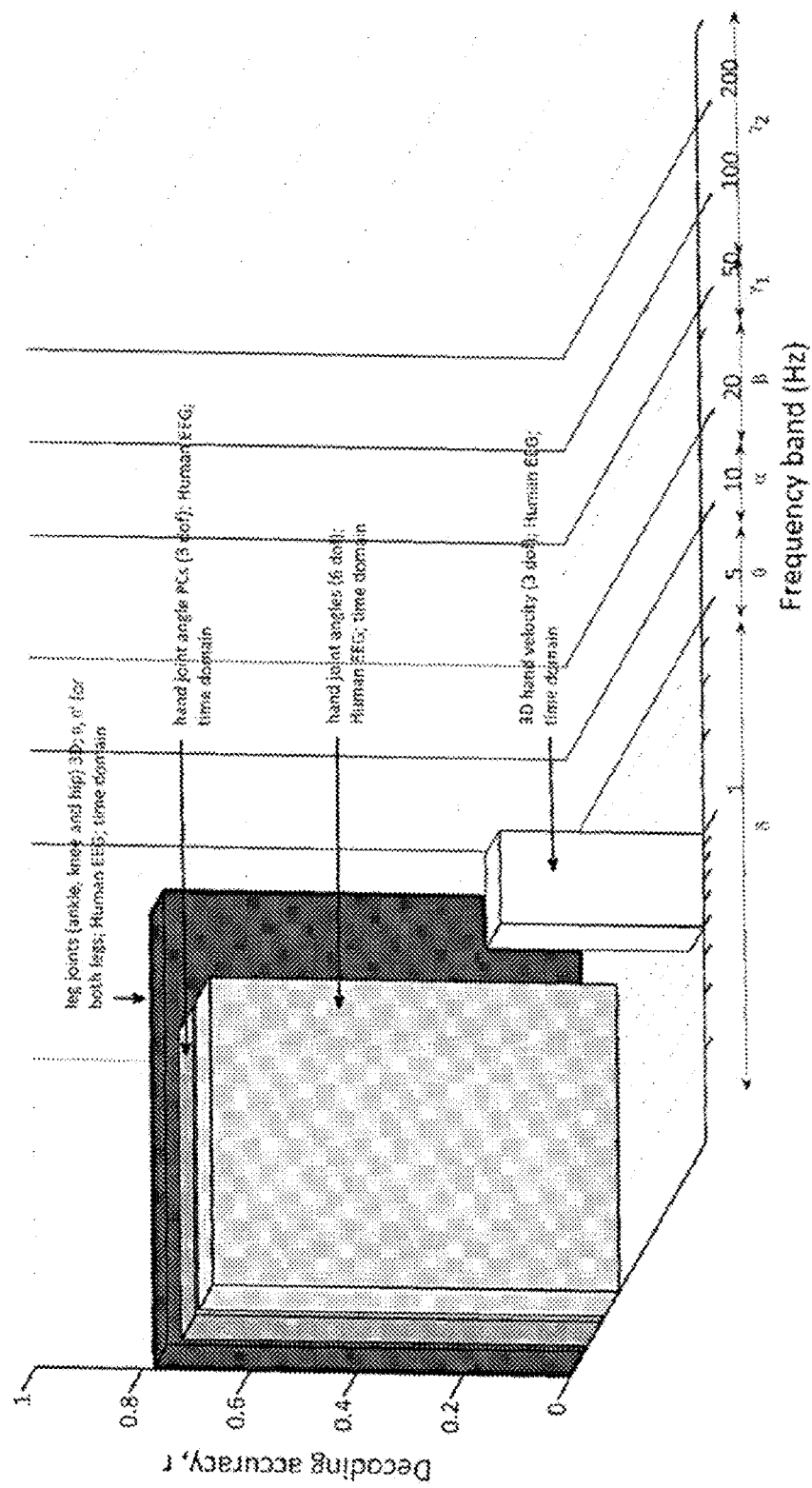
FIG. 23 illustrates graphically decoding accuracy versus frequency content of input features in studies for decoding human bipedal locomotion data and decoding hand grasping and hand reaching data according to methods of the present invention. As shown, the data is based on noninvasively acquired EEG signals in the delta ($\delta$) band (<4 Hz) and in the time-domain. Utilizing the time domain and lower frequency signals, a relatively high decoding accuracy is achieved that is comparable or better than the decoding accuracies reported in invasive decoding methods. The decoding accuracy is the Pearson's correlation coefficient (r) between the predicted and observed trajectories. Annotations on bars describe the kinematic parameters being decoded, the modality of the neural signal acquisition, the number of decoded degrees-of-freedom (dof), the input feature space (time/frequency domain). The illustrated studies were performed on humans. On the frequency axis, range of the functional bands ($\delta$, $\theta$, $\alpha$, $\beta$, $\gamma_1$, $\gamma_2$) is shown. All studies use Wiener filter as a decoder, although other decoder types such Kalman filter may also be utilized. The inclusion criteria for the studies are: 1) continuous time; 2) continuous movement space (as opposed to discrete targets); and 3) decoding of direct movement parameters (as opposed to cursor control on a computer screen).

The EEG decoding method reconstructed 3D hand-velocity profiles reasonably well. The decoding accuracy was quantified by computing the mean of Pearson's r between measured and reconstructed hand velocity across cross-validation folds. For y and z velocities, the decoding accuracy peaked at 0.38 and 0.32, respectively, with only 34 sensors (FIG. 11, Panels A and B; see also FIG. 23). For x velocity with 34 sensors, the decoding accuracy of 0.19 remained relatively unaffected by the number of sensors. Thus, we used 34 sensors for subsequent analyses. In addition to quantitatively analyzing decoding accuracy, visually comparing reconstructed and measured velocity profiles confirmed their similarities (FIG. 11, Panel C).

Figure 12:
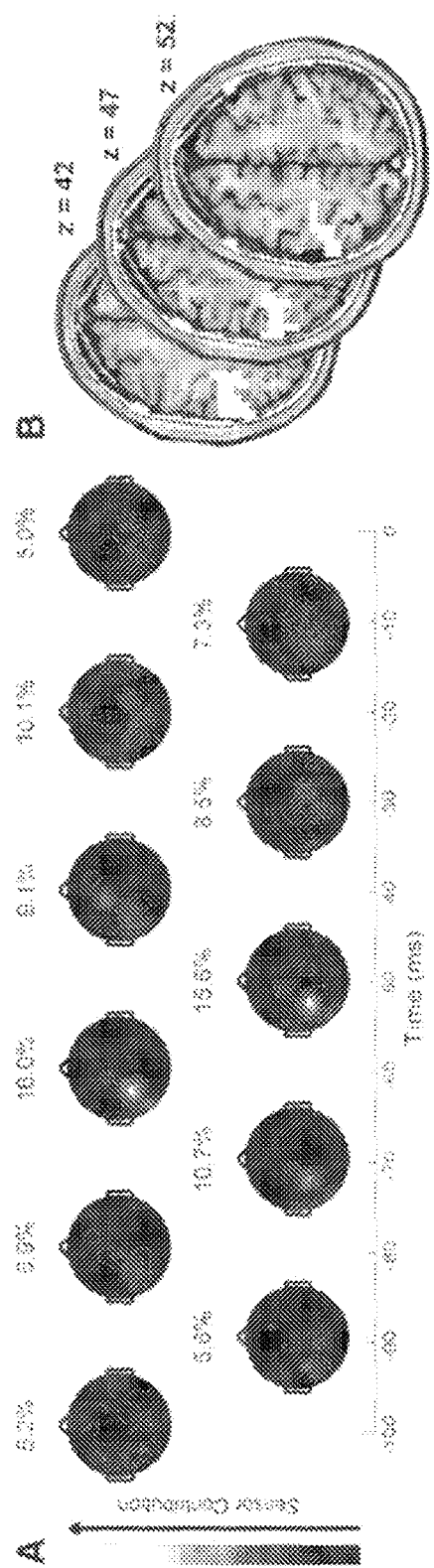
FIG. 12 illustrates scalp maps and current sources that encoded hand velocity of the second embodiment. Shown in Panel A, mean (n=5) scalp maps of the best 34 sensors revealed a network of frontal, central, and parietal involvement along with a large individual contribution from sensor CP3. Light and dark colors represent high and low contributors, respectively. Each scalp map with its percentage contribution is displayed above its associated 10 ms time lag, revealing the 16.0% maximal contribution of EEG data at 60 ms in the past. In Panel B, localized sources (yellow) from 60 ms in the past were overlaid onto MRI structural images to reveal the involvement of the precentral gyrus (x=−30, y=−30, z=52), postcentral gyrus (x=−35, y=−30, z=47), and IPL (x=−35, y=−36, z=42).

Referring to FIG. 12, Panel A, scalp maps depicted the contributions of the 34 sensors as a network of frontal, central, and parietal regions. Within this network, sensor CP3 made the greatest contribution. Interestingly, CP3 lies roughly above the primary sensorimotor cortex that is contralateral to the reaching hand. Concerning time lags, EEG data from 60 ms in the past supplied the most information with 16.0% of the total contribution. At 60 ms, we localized the EEG sources to confirm that the primary sensorimotor cortex (precentral gyrus and postcentral gyrus) was indeed a major contributor along with the inferior parietal lobule (IPL) (FIG. 12, Panel B).

Figure 13:
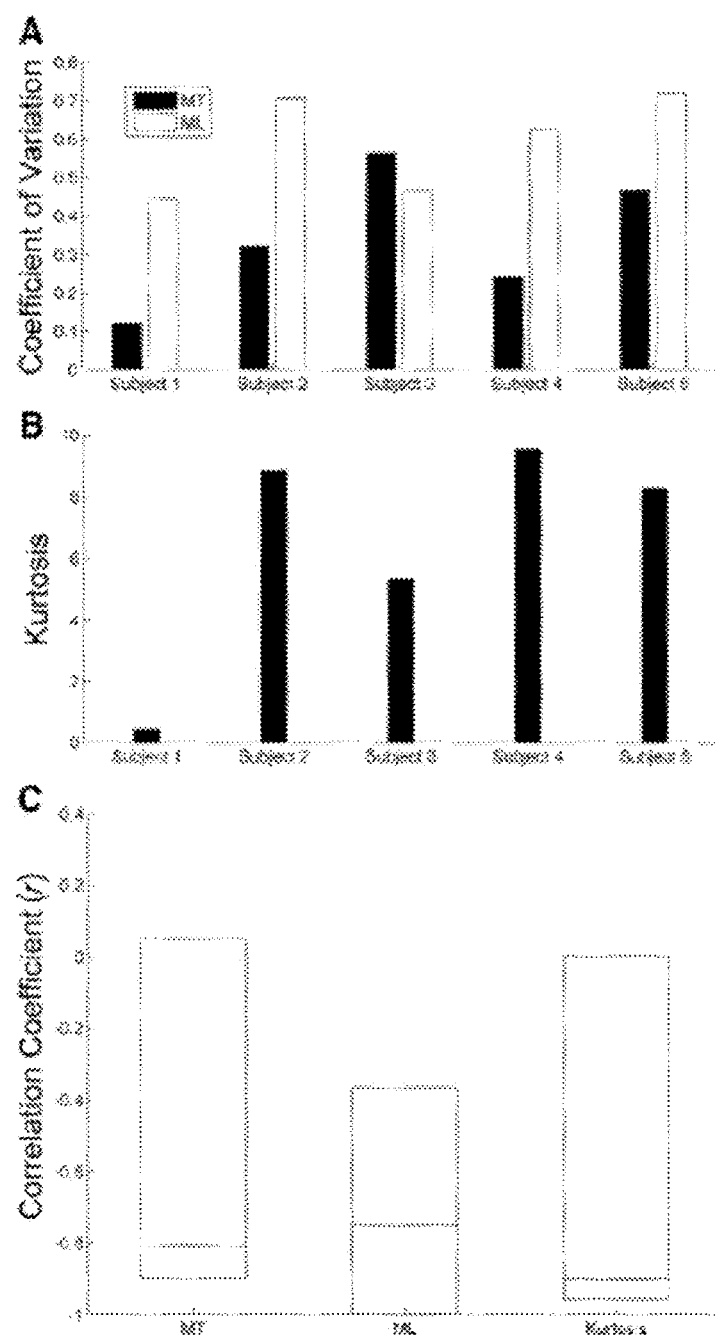
FIG. 13 illustrates graphically the relationship between movement variability and decoding accuracy of the second embodiment. Shown in Panel A, the CVs for MT (black) and ML (white) ranged across subjects. As shown in Panel B, the kurtosis of the velocity profiles also varied across subjects. As shown in Panel C, all movement variability measures demonstrated high negative correlations with the decoding accuracy shown in FIG. 11, Panel B. Rectangles demarcate the confidence intervals for the bootstrapped r values, with each rectangle possessing a horizontal line at the median. The confidence intervals are 70, 90, and 70%, respectively, for MT, ML, and kurtosis.

Additionally, we compared the relationship between decoding accuracy (FIG. 11, Panel B) and movement variability. To quantify movement variability, we computed the CV for MT and ML (FIG. 13, Panel A) and the kurtosis of the velocity profiles (FIG. 13, Panel B). The high kurtosis values indicated outlier-prone, super-Gaussian distributions (kurtosis, >0). We found that movement variability negatively correlated with decoding accuracy (FIG. 13, Panel C).

Discussion

In the BCI system according to the second embodiment, we continuously reconstructed 3D hand velocity of natural, multi-joint, center-out movements from only 34 channels of EEG data. A sensorimotor network composed of frontal, central, and parietal scalp regions encoded for hand velocity, with the strongest contributions coming from cortical regions of the precentral gyrus, postcentral gyrus, and IPL at 60 ms in the past. Furthermore, the intersubject variability in movement may explain the intersubject variability in decoding accuracy due to their negative correlation.

The sensor sensitivity curves for y and z velocities peak at ~0.35 for 34 sensors before they begin decreasing. A common occurrence in machine learning is that, as the number of input features increases, prediction increases up to a point, then prediction may decrease due to overfitting the model to the training data (Alpaydin (2004) "Introduction to machine learning," p. 54, Cambridge, Mass., MIT).

The curve for x velocity remains nearly flat ~0.20 after an initial rapid increase (FIG. 11, Panel A). An assumption was made that the brain employs a hand-centered Cartesian coordinate system. However, the possibility exists that the brain could represent a different coordinate system (e.g., joint space or multiple interacting frames of reference) or desired muscular activity (Gourtzelidis et al. (2001) "Systematic errors of planar arm movements provide evidence for space categorization effects and interaction of multiple frames of reference," Exp. Brain Res., 139:59-69; Wu et al. (2006) "Evidence against a single coordinate system representation in the motor cortex," Exp. Brain Res., 175:197-210; Wu et al. (2007) "Coordinate system representations of movement direction in the premotor cortex," Exp. Brain Res., 176:652-657). The dimensions of an alternate representation could correlate better with y and z velocities than x velocity, potentially explaining the uniqueness of the sensitivity curve for x velocity. Nonetheless, in future studies when subjects are asked to use motor imagery to control a cursor or virtual arm in 3D via our decoder, it is expected that their neural activity would adapt to overcome an initial imperfect choice of representation framework (Ganguly et al. (2009) "Emergence of a stable cortical map for neuroprosthetic control," PLoS Bio., 7:e1000153).

Comparison to Other BCI Methods

No other comparable studies on continuously decoding hand kinematics from EEG exist. However, two studies report off-line, continuous reconstruction of 3D hand kinematics from intracranial neuronal activity (Wessberg et al. (2000), supra, Nature, 404:361-365; Kim et al. (2006), supra, J. Neural Eng., 3:145-161), and several studies report off-line, continuous reconstruction of 2D hand and tool kinematics from MEG (Georgopoulos et al. (2005), supra, Exp. Brain Res., 167:132-135; Jerbi et al. (2007), supra, Proc. Natl. Acad. Sci. USA, 104:7676-7681; Bradberry et al (2008), supra, Conf. Proc. Eng. Med. Biol. Soc. 2008:5306-5309; Bradberry et al. (2009a), supra, Neuro-image, 47:1691-1700). Of the MEG investigations, exclusive employing a center-out movement paradigm, the de facto standard for comparison among decoding studies with BCI implications. These other studies report slightly higher r values, but uniquely the present method involves more ambitious experimental settings, such as more reaching targets, greater extent of multi-joint movements, self-initiated movements, and self-selected targets.

Further, the resulting scalp maps and estimated current sources indicate involvement of the contralateral primary sensorimotor region and the IPL. Other studies confirm that the primary sensorimotor cortex encodes hand kinematics at a microscale (Moran et al. (1999) "Motor cortical activity during drawing movements: population representation during spiral tracing," J. Neurophysiol., 82:2693-2704; Wessberg et al. (2000), supra, Nature, 404:361-365; Serruya et al. (2002), supra, Nature, 416:141-142; Schwartz et al. (2004) "Differential representation of perception and action in the frontal cortex," Science, 303:380-383; Kim et al. (2006), supra, J. Neural Eng., 3:145-161), mesoscale (Schalk et al. (2007), supra, J. Neural. Eng., 4:264-275; Pistohl et al. (2008), supra, J. Neurosci. Methods, 167:105-114; Sanchez et al. (2008), supra, J. Neurosci. Methods, 167:63-81), and macroscale (Kelso et al. (1998) "Dynamic cortical activity in the human brain reveals motor equivalence," Nature, 392: 814-818; Jerbi et al. (2007), supra, Proc. Natl. Acad. Sci. USA, 104:7676-7681). Several MEG studies report that the IPL also encodes hand kinematics (Jerbi et al. (2007), supra, Proc. Natl. Acad. Sci. USA, 104:7676-7681; Bradberry et al. (2009a), supra, Neuro-image, 47:1691-1700). Regardless of scale, the decoding methods disclosed herein rely on a subsecond history of neural data to reconstruct hand kinematics (Serruya et al. (2002), supra, Nature, 416:141-142; Sanchez et al. (2008), supra, J. Neurosci. Methods, 167:63-81; Bradberry et al. (2009a), supra, Neuro-image, 47:1691-1700). The choice of a 100 ms lag aligns with this convention as well as the rationale that these lags consist of planning activity of the brain associated with the current kinematic sample of the hand. Furthermore, across lags the sensor contributions initially increase, peak at 60 ms, and then decrease, possibly revealing a temporal tuning curve for our task. Since only low-frequency components of the EEG signals seem to carry information about hand velocity, slow cortical potentials emerge as the best candidates for a neurophysiological interpretation of these findings (Birbaumer et al., 1990).

One aspect of BCI research involves how decoding methods may adapt or facilitate user adaptation to novel environments or cognitive states. To evaluate adaptation, the user of a BCI system must receive feedback (e.g., visual or kinesthetic) of imagined movements while manipulating a brain-controlled device in real time. In the future, it will be advantageous to provide subjects with real-time feedback to investigate their ability to adapt their EEG activity to a fixed decoder (i.e., test the ability of our decoder to generalize). To improve performance, it is expected that subjects will "modify" regression weights by modulating their EEG activity.

Regarding the negative correlation between movement variability and decoding accuracy, two potential explanations are proposed. Increased movement variability could degrade decoding accuracy due to less similar pairs of EEG-kinematic exemplars. Conversely, less movement variability results in more similar exemplars for training. Alternatively, subjects differ in their ability to perform the task without practice; hence, the strengths of a priori neural representations of the required movements differ. These differing strengths could directly relate to the accuracy with which the representations can be extracted. Indeed, a previous study confirms that motor learning produces more accurate predictions of movement direction from an ensemble of neuronal activity in primary motor cortex (Cohen et al. (2004) "*Reduction of single-neuron firing uncertainty by cortical ensembles during motor skill learning*," J. Neurosci., 24:3574-3582). This finding is important to consider as real-time BCI systems based on our decoder are further investigated.

In conclusion, the disclosed methods demonstrate that EEG signals possess decodable information about detailed, complex hand movements.

An EEG-based BCI system according to a third embodiment uses neural activity as inputs and provides control signals to drive desired gesture formation in neuromotor prosthetic or orthotic hands. The input neural activity comprises multichannel macro-scale neural signals. Examples of such techniques to record neural signals are local field potentials (LFPs), ECoG, EEG and MEG signals. The method uses a specific input feature space and a specific optimization procedure to determine the best subset of input channels, along with a decoded module that performs a linear transformation on the inputs to produce the desired kinematic trajectories for each degree of freedom to be controlled. An example experiment of a BCI system according to the third embodiment is provided:

EXAMPLE 3

Methods and Materials

Five healthy, right-handed subjects sat upright in a chair and executed self-initiated, center-out grasping tasks. In particular, the subjects were seated behind a table with five objects (calculator, CD, espresso cup, zipper and a beer mug) arranged in front of them in a semicircle with an approximate radius of 30 cm. The initial position of the hand was palm down and flat on the table at the center of the semicircle. On the presentation of an auditory "go" cue (100 ms tone at 2 kHz), the subjects were instructed to select, reach out and grasp any of the five objects. Subjects kept a steady grasp on the objects until an auditory "stop" cue (200 ms tone at 1 kHz) was presented 5 s after the "go" cue, on hearing which they returned their hand to the resting initial position.

The time until the presentation of the "go" cue for the next trial was Gaussian distributed with a mean of 7 s and standard deviation of 1 s. Five blocks of 12 minutes each were recorded for subjects S1, S2 and S3 and four blocks were recorded for subjects S4 and S5. 50 trials were recorded in each block on average. At the end of each block, the placement of the five objects was rotated clockwise so as to provide a plurality of reach directions for grasping the same object, ensuring that eye movements did not play a role in decoding.

EEG signals and hand kinematics were recorded simultaneously while subjects performed the grasping task. Whole head EEG was recorded using a 64-sensor cap for sensing EEG signals (such as described above). The acquired signals were amplified and digitized at 500 Hz with a Net Amps 300 acquisition system (available from Electrical Geodesics, Inc. of Eugene, Oreg.). The trajectories of 23 joint angles were recorded with a wireless data glove including flexion finger sensors, abduction sensors, a palm-arch sensor, and/or sensors to measure wrist flexion and abduction (such as available from CyberGlove Systems, LLC of San Jose, Calif.) at a resolution of 0.93° at a non-uniform sampling rate of 35-70 Hz.

Preprocessing

In this example, all analyses were performed offline using custom built programs in MATLAB (available from Mathworks Inc. of Natick, Mass.). The raw synchronized EEG and kinematics were down-sampled to 100 Hz following the application of a Chebychev type-II antialiasing filter at 40 Hz. The raw kinematics were interpolated with a piecewise cubic hermite interpolating polynomial and up-sampled to 100 Hz. After rejecting 18 peripheral EEG channels and channels with high impedances (greater than 200 k$\Omega$), EEG was re-referenced to a common average (CAR). EEG was then high pass filtered at 0.1 Hz with a zero-phase 4th order Butterworth filter. Next, both EEG and kinematics were low-pass filtered (LPF) at 1 Hz with a zero-phase first order Butterworth filter. All EEG channels were standardized by their respective means and standard deviations. The continuous EEG and kinematics were segmented into trials consisting of the movement period from 0.5 s before movement onset to 2.5 s after movement onset. Any data outside of the movement periods were discarded. The segmentation was done to provide a balanced representation of movement and rest periods for the purpose of training the decoder. Movement onsets were determined to be points at which the joint angle speed exceeded 5% of the maximum during a trial for the first time. The segmented data were baseline corrected using a baseline of −0.5 s to 0 s with respect to movement onset.

Linear Decoding Model

Figure 14:
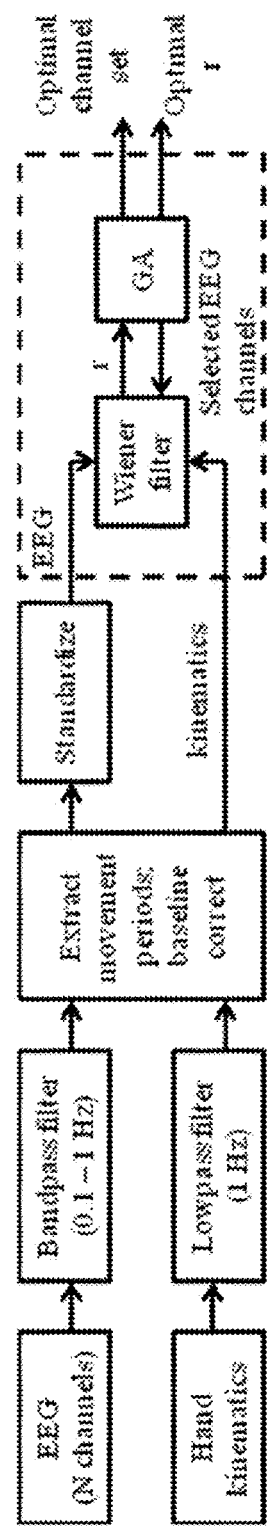
FIG. 14 is a flowchart showing a decoder block diagram of an EEG-based BCI system according a third embodiment. Preprocessed EEG and kinematics is passed to the decoder module (shown as a dashed box), containing the linear decoder and a genetic algorithm (GA) based wrapper. The GA wrapper maximizes the correlation coefficient (r) between the observed and predicted kinematics.

The decoding approach is illustrated schematically in FIG. 14. EEG channels to be used for decoding were selected based on an evolutionary optimization procedure (described in the next section). Each of the movement variables was independently modeled as a linear combination of data from the selected sensors:

$$y[t] = \beta_0 + \sum_{i \in \psi} \beta_i S_i[t + \Delta]$$

where y[t] is the joint angle time-series being decoded at time t, $\beta_0$ are the model parameters, $S_i$ are the sensor values for the ith sensor, $\Delta$ denotes the time delay (lag) between EEG and kinematics, and $\psi$ is the optimal set of EEG sensors. Model parameters were calculated using the Generalized Linear Model (GLM). The model was validated using 10-fold cross-validation (i.e., 10 distinct sets of test data that were not used to train the decoder). The predictive power of the decoding model (decoding accuracy) was designated to be the median value of the Pearson correlation coefficient (r) between the observed and predicted kinematics across the 10 folds.

Selection of Optimal Sensors

To optimize the neural decoder, a genetic algorithm was employed to select the EEG channels to be used as inputs to the linear decoder. The genetic algorithm is a search heuristic inspired by the process of natural evolution, and which provides a global optimization strategy to search the input space in a directed manner. The first generation was initialized to a population of 22 individuals with randomly chosen EEG channels. The fitness of each individual, defined as the median decoding accuracy across the 10 cross validation folds, was evaluated. The 2 best individuals in the population were selected to survive to the next generation unchanged. 16 individuals in the next generation were created using crossovers between the individuals of the current generation. The remaining 4 individuals were mutated from individuals in the current generation. The mutation rate was set to an average of 2 channels in each individual. The algorithm was allowed to run for a maximum of 500 generations or until a convergence criterion was met, whichever happened earlier. The convergence criterion was satisfied if the cumulative change in the fitness function over the last 100 generations was less than $10^{-12}$.

Decoding Accuracy Results

Figure 15:
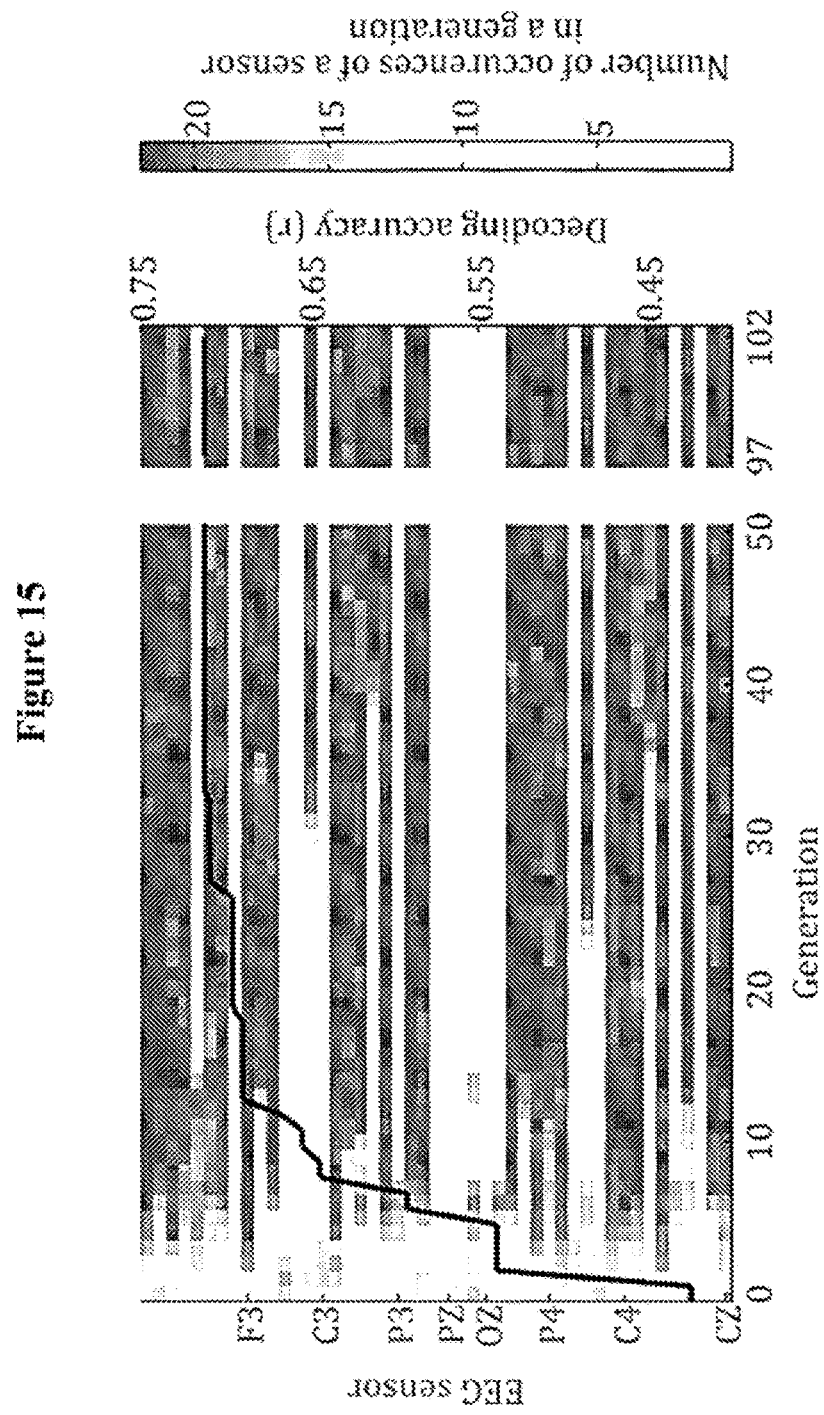
FIG. 15 illustrates the evolution of the genetic algorithm according to the third embodiment across generations (x-axis). EEG channels are shown along the y-axis. Selectivity of channels across individuals in a generation is color coded. At the onset of the optimization, channels are chosen randomly (low selectivity) but quickly converge onto a subset of channels (high selectivity channels), which gives the optimal decoding accuracy. The black trace line shows the improvement in the decoding accuracy as the algorithm converges.
Figure 16:
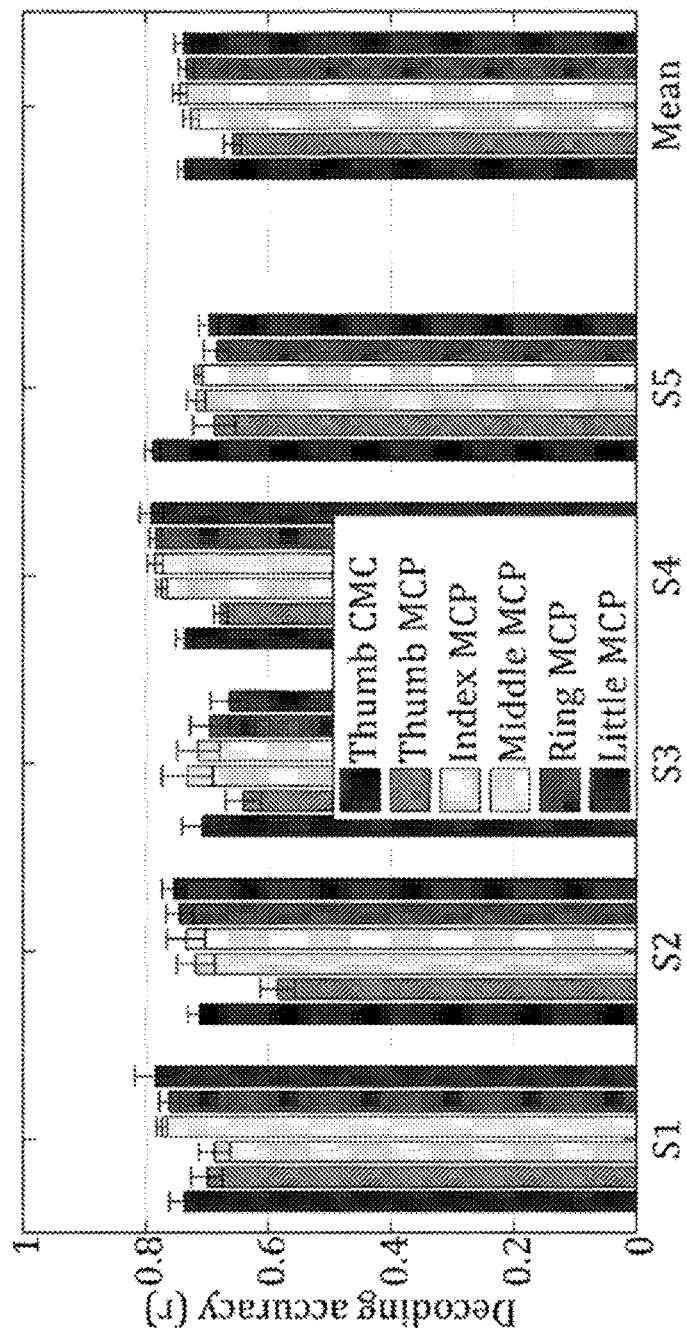
FIG. 16 illustrates graphically a summary of decoding accuracy for joint angle prediction according to the third embodiment. The first five bar groups show r values for the five subjects for each of the joints. For each group, the five bars (from left to right) represent values for: the thumb carpometacarpal (CMC) joint (CMC); the thumb metacarpophalangeal (MCP) joint; the index finger MCP joint; the middle finger MCP joint; the ring finger MCP joint; and the little finger MCP joint. The sixth group shows the mean across all subjects. Error bars indicate standard error of the mean.
Figure 17:
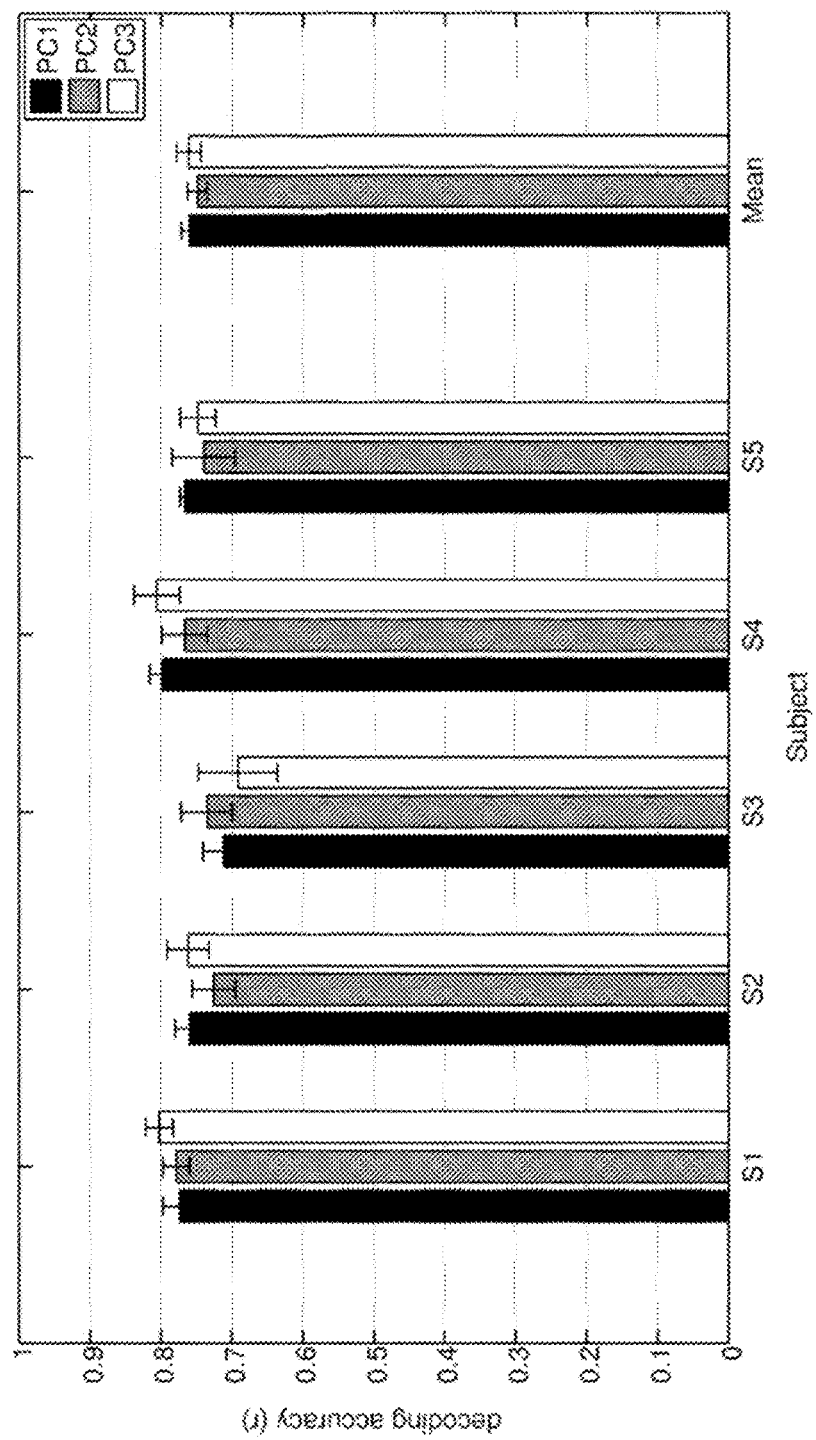
FIG. 17 depicts graphically a summary of decoding accuracy joint angle principal component prediction according to the third embodiment. The first five bar groups show r values for the five subjects for each of the three principal components. The sixth group shows the mean across all subjects. Error bars indicate standard error of the mean.

Referring to FIG. 15, the improvement in the decoding accuracy as the genetic algorithm converges onto an optimal subset of EEG electrodes is shown, for an example trial. A summary of the results for various joint angles for all subjects is illustrated in FIG. 16. These results illustrate a specific example of decoding joint angle time-series from EEG. However, other kinematic parameters could also be decoded, such as joint angular velocity and acceleration, in the same manner. Principal component analysis is a commonly used method to capitalize on the coordinated movements of fingers while performing gestures by concentrating the correlated variability in finger movements in a small number of principal components. FIG. 17 shows the results of decoding by applying the disclosed method to decode principle components during gesture formation.

The disclosed method enables the extraction of movement kinematics during hand gesture motion from noninvasive scalp EEG signals. An actuator of the present invention is thus capable of using the decoded hand kinematic parameters (e.g., cartesian X,Y,Z time series representing the movement of each joint of the hand, or alternatively the joint position or velocities of each joint of the hand) to actuate a prosthetic.

Thus, the EEG-based BCI system according to the third embodiment utilizes neural activity as inputs and provides control signals to drive desired gesture formation in neuromotor prosthetic or orthotic hands. The disclosed method uses a specific input feature space and a specific optimization procedure to determine the best subset of input channels, along with a decoded module that performs a linear transformation on the inputs to produce the desired kinematic trajectories for each degree of freedom to be controlled.

A EEG-based BCI according to a fourth embodiment provides for noninvasive decoding of human bipedal locomotion patterns from noninvasive scalp EEG signals alone that can achieve brain-machine confluence. The disclosed BCI system is based on neural source signals correlated with behavioral variables (e.g., linear or angular movement kinematics such as three-dimensional Cartesian or angular positions of joints and segments constituting the human legs). The resulting BCI system substantially reduces training time required, while allowing confluence between the brain and the robotic exoskeleton.

The disclosed method employs noninvasive, multichannel scalp EEG neural signals to decode, reconstruct or predict human bipedal locomotion patterns. The decoded locomotion signals can be utilized to command a wearable leg exoskeleton to restore lower limb motor functions such as walking and running in individuals with gait deficits or injury, to retrain gait patterns in these individuals, or to enhance motor performance in able individuals.

In one implementation, the neural signals acquired with a multichannel EEG system are processed with the disclosed method to generate desired walking control signals that can be utilized to command a robotic exoskeleton, worn outside the body and comprised of a pair of robotic legs, thus enabling a paralyzed individual or an individual with locomotion deficits to walk, move sideways, turn around, or go up and down steps. In another implementation, the decoded neural signals can be utilized to remotely control a robot (e.g., a walking robot) in space or earth.

An example experiment of a BCI system according to the fourth embodiment is provided:

EXAMPLE 4

Methods and Materials

A male subject walked on a treadmill at his self-selected comfortable speed for 5 minutes, while bilateral 3D joint kinematics obtained from an optical measurement system (such as available from Northern Digital, Inc. of Ontario, Canada) and foot switch data obtained from sensor instrumentation (such as available from Koningsberg Instrumentation, Inc. of Pasadena, Calif.) were collected at a sampling rate of 100 Hz.

The subject wore a whole head 64-sensor cap for sensing EEG signals (such as available from Compumedics USA of Charlotte, N.C.). Electro-ocular activity was also recorded (at 500 Hz, band-pass filtered from 0.1 to 100 Hz, right ear lobe (A2) as the reference) and time-locked with the movement kinematics using the footswitch signals.

Figure 18:
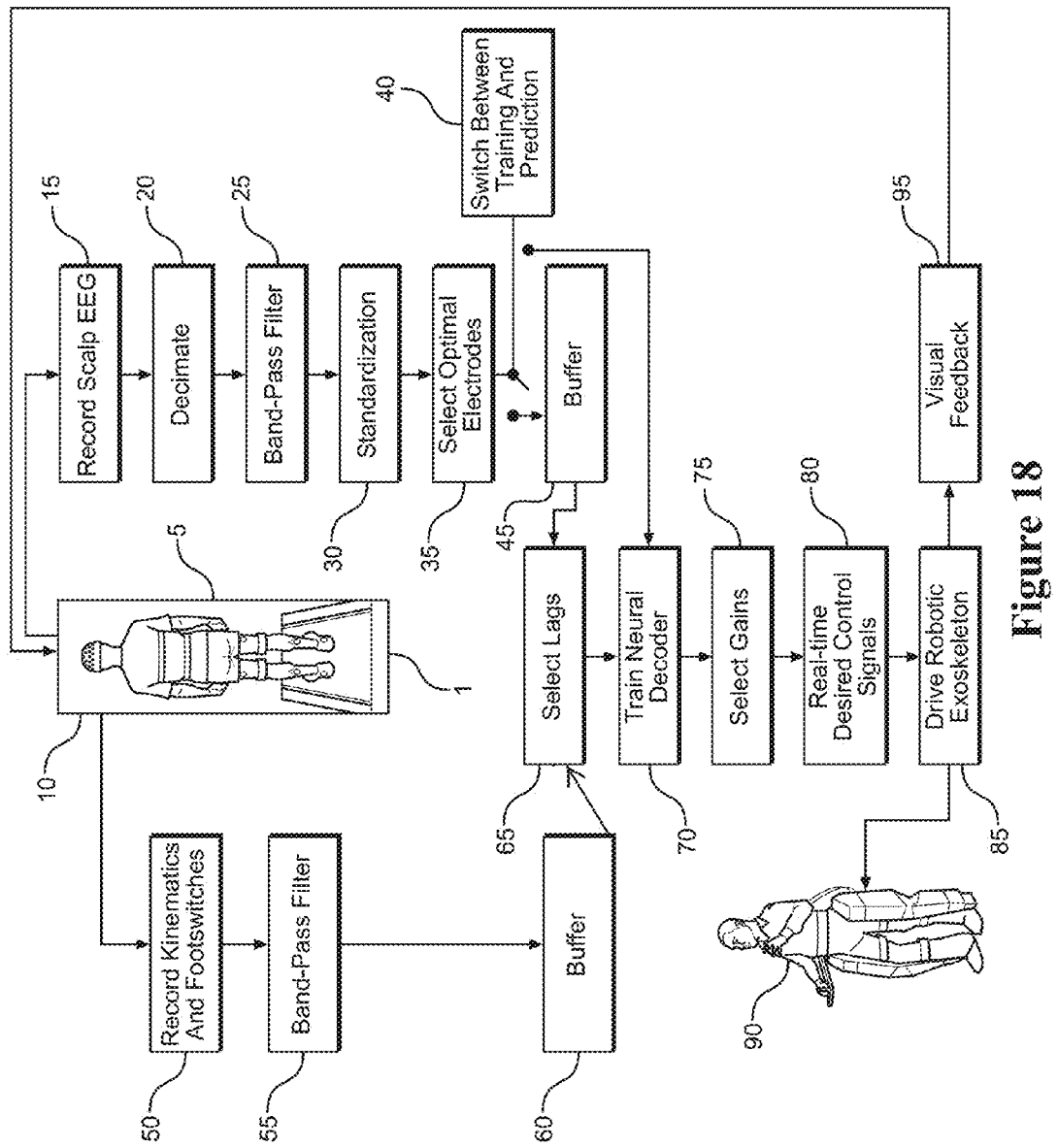
FIG. 18 is a schematic flowchart illustrating a BCI system according to a fourth embodiment for controlling a wearable lower limb exoskeleton. The subject is wearing a high-density EEG cap to record brain activity and a plurality of sensors used to record 3D joint kinematics and footswitch data. EEG and kinematics are synchronized and saved for off-line analysis (e.g., training the neural decoder). Once trained, the neural decoder may be used in real-time to control the robotic exoskeleton.

An exemplary setup of the BCI system according to the present invention is illustrated in FIG. 18. The subject 1 wears a high-density EEG cap 10 to noninvasively record the brain activity 15 and a plurality of sensors 50 to record the kinematics and footswitches patterns. Before being stored in the buffer 45, EEG data are decimated 20, band-pass filtered 25, and normalized with respect to the mean and standard deviation 30. Optimal electrodes for signal prediction are selected 35. Kinematics are stored in a buffer 60 after being band-pass filtered 55. During a calibration phase in which the neural decoder is trained (cf. a switch is used to change between training and prediction modes 40), the subject walks on a treadmill 1 at his self-selected comfortable speed for 5 minutes. The kinematic and EEG data stored in the buffers are then used to train the decoder 70 with selected lags 65. If necessary, a gain 75 is applied to the output of the decoder during performance in signal prediction mode chosen with switch 40. Real time predictions 80 representing desired control signals can be used to control devices 85, such as a robotic exoskeleton 90 (available from RexBionic of North Shore City, New Zealand). Feedback 95 is sent back to the subject using a visual display.

Signal Processing

In this laboratory example, all the data analysis and decoder training was performed off-line. EEG was aligned with the kinematics and down-sampled from 500 Hz to 100 Hz. Electrodes that played a minimal or no role in the decoding of human walking (e.g., T14, T5), or that might have been affected by artifacts (e.g., eye artifacts; Fpz, etc.) were removed from analysis. Additionally, an inspection of all the remaining electrodes were performed in order to eliminate noisy sensors. A zero-phase, third order, band-pass Butterworth filter (0.1-3 Hz) was applied to the kinematics, while a zero-phase, third order, band-pass Butterworth filter (0.1-2 Hz) was applied to the EEG data. Finally, EEG data were standardized with respect to the mean and standard deviation. All analyses were performed using custom programs written in MATLAB (MathWorks Inc. of Natick, Mass.).

Decoding Method

To decode gait trajectories from EEG signals, a time-embedded (10 lags, corresponding to 100 ms in the past) linear regression model or Wiener filter was used (Bradberry et al. (2010), supra, J. Neurosci. 30:3432-3437):

$$y(t) = a + \sum_{n=0}^{N} \sum_{k=0}^{L} b_{nk} S_n(t-k),$$

where y(t) is the kinematics recorded, L and N are respectively the number of lags and the number of sensors, $S_n(t-k)$ is the standardized difference in voltage measured at EEG sensor n at lag time k and the a and b variables are weights obtained through multiple linear regression.

Selection of the Electrodes for the Decoding

Sensor sensitivity curves depicting the relationship between decoding accuracy and the number of sensors used in the decoding method were plotted for the x,y,z movement dimensions for each joint. The sensors were ranked based on the following equation (Bradberry et al. (2010), supra, J. Neurosci. 30:3432-3437):

$$R_n \frac{1}{L+1} \sum_{k=0}^{L} \sqrt{b_{nkx}^2 + b_{nky}^2 + b_{nkz}^2},$$

where L is the number of lags, $R_n$ is the rank of sensor n and the b variables are the best correlation coefficients for each Cartesian position (x,y,z). Electrodes were then shuffled in order to evaluate the robustness of this method.

Model Performance Metrics

In order to assess and compare the predictive power of the decoder, a 5-fold (leave-one-out) cross validation procedure for each subject and condition. For instance, the data were divided into 5 equal segments (5-folds). Each of the first 4 segments (first 80% of the recorded EEG) was used to train the neural network, resulting in 4 different neural networks. The mean Pearson correlation coefficient (r) was then calculated between the 4 neural networks and the last segment (last 20% of the recorded EEG) as follows:

$$r(x, \hat{x}) = \frac{\text{cov}(x, \hat{x})}{\sigma_x \sigma_{\hat{x}}}$$

The SNR (signal to noise ratio) was calculated as follows (Fitzsimmons et al. (2009)):

$$SNR(x, \hat{x}) = 10 \log_{10}\left(\frac{\text{Var}(x)}{MSE(\hat{x})}\right)$$

where the variance of the actual variable that was predicted (signal x) was calculated by subtracting out the mean of the signal, then squaring and averaging the amplitude. The noise or error ($\hat{x}$) was the difference between the extracted and actual signal. The error was calculated by subtracting the actual parameter from the extracted parameter, squaring the difference, then averaging to get the mean squared error (MSE), or the power of the noise. The ration between Var(x) and MSE($\hat{x}$) was then converted in decibel (dB) scale.

Decoder Accuracy Results

Figure 19:
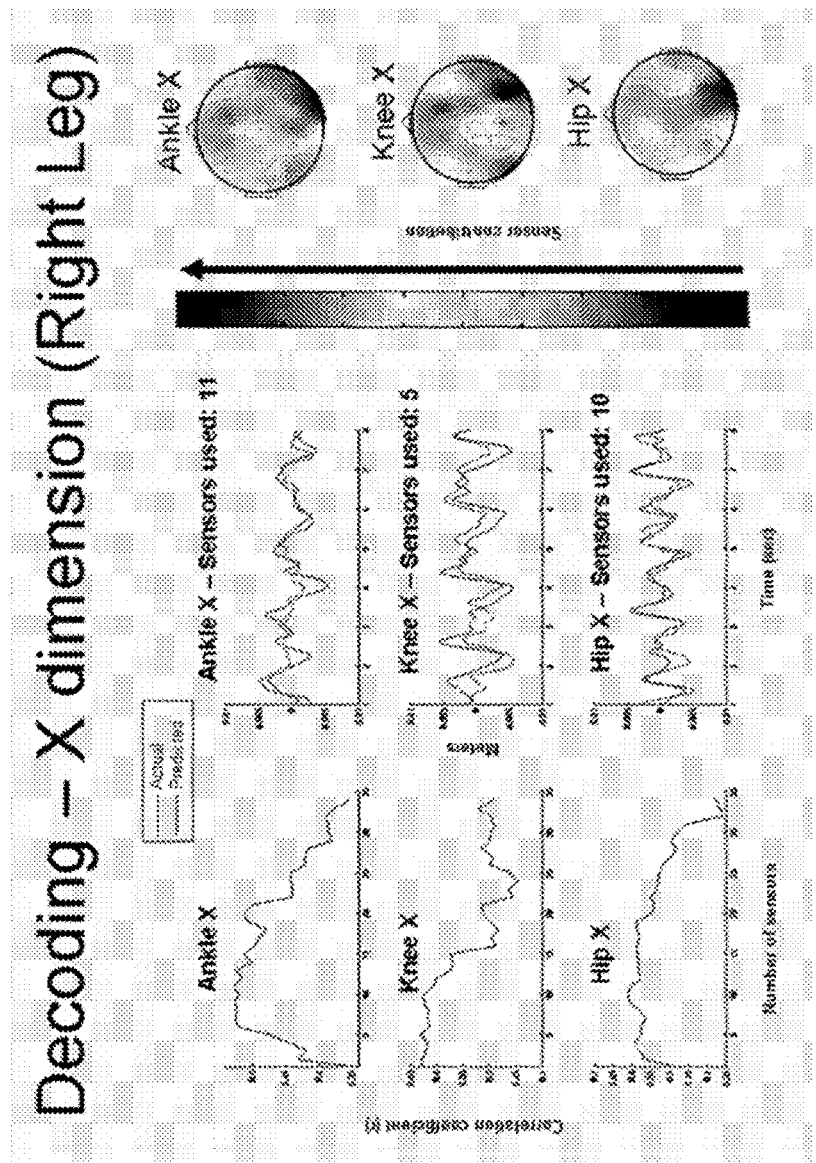
FIG. 19 illustrates graphically decoding results and scalp maps for decoding of movement along the "x" axis according to the fourth embodiment. The 3 plots on the left end side show the Pearson's correlation values (r) with the first 34 best sensors. The 3 plots in the middle show the actual versus the predicted signals. Scalp maps represent the correlation (decoding accuracy) for each joint.
Figure 20:
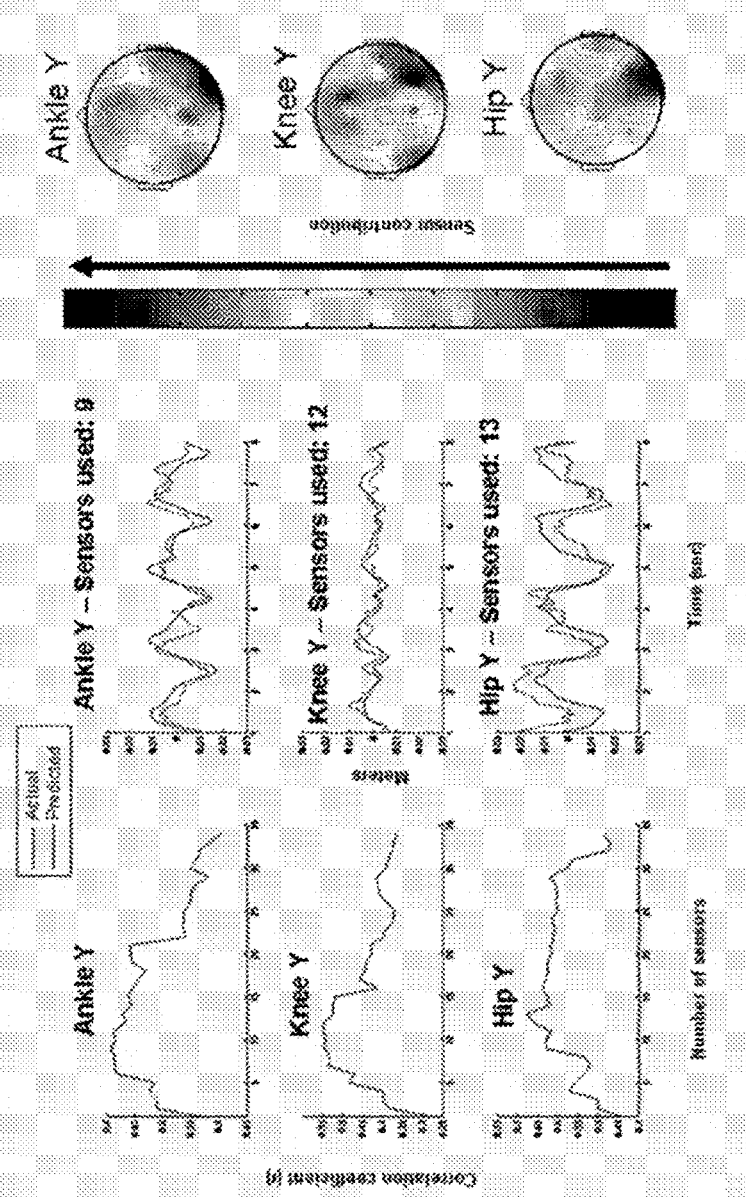
FIG. 20 illustrates graphically decoding results and scalp maps for decoding of movement along the "y" axis according to the fourth embodiment. The 3 plots on the left end side show the Pearson's correlation values (r) with the first 34 best sensors. The 3 plots in the middle show the actual vs. the predicted signals. Scalp maps represent the correlation (decoding accuracy) for each joint.
Figure 21:
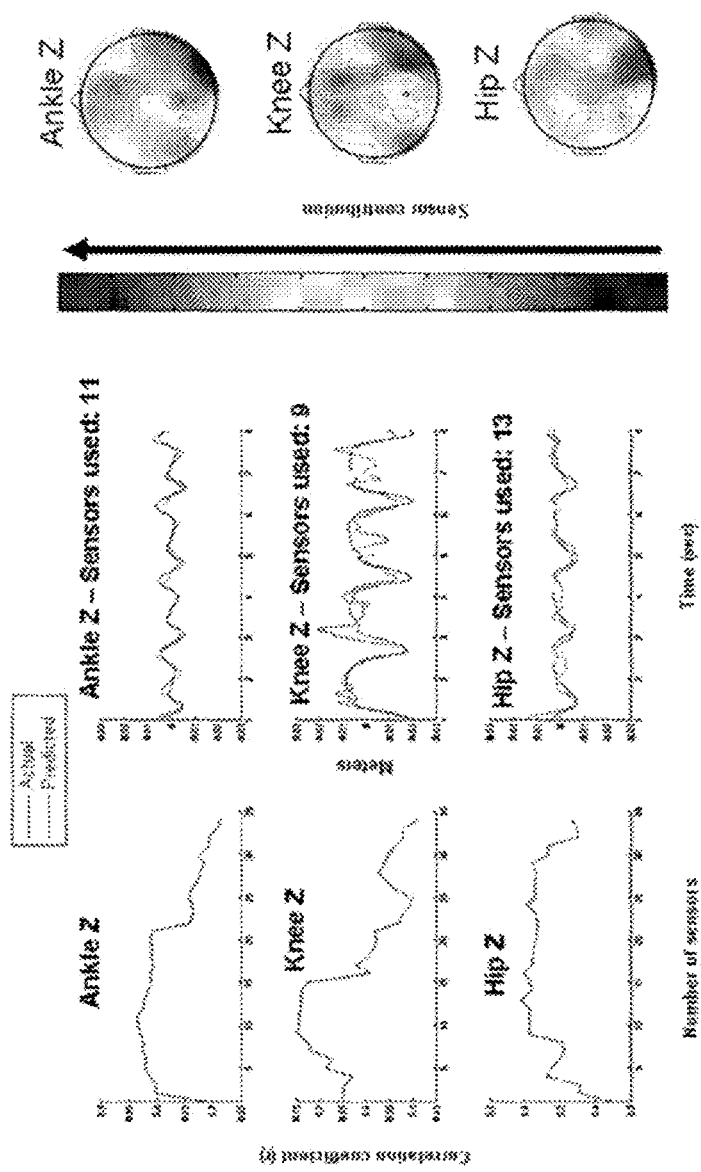
FIG. 21 illustrates graphically decoding results and scalp maps for decoding of movement along the "z" axis according to the fourth embodiment. The 3 plots on the left end side show the Pearson's correlation values (r) with the first 34 best sensors. The 3 plots in the middle show the actual vs. the predicted signals. Scalp maps represent the correlation (decoding accuracy) for each joint.
Figure 22:
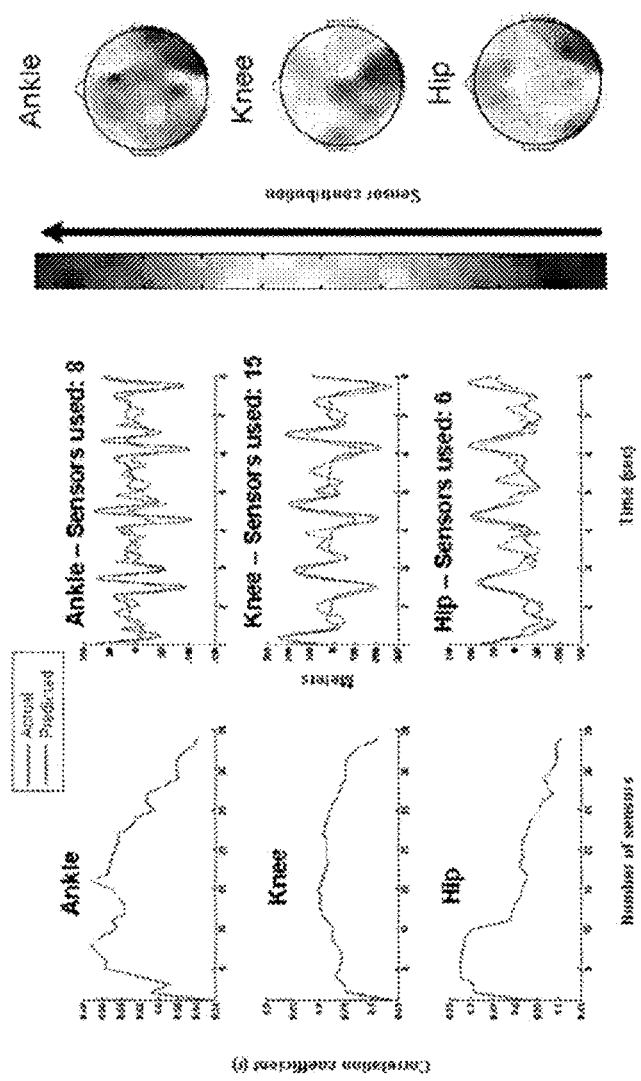
FIG. 22 illustrates decoding results and scalp map for angular velocities for the ankle, knee, and hip joints of the right leg according to the fourth embodiment. The 3 plots on the left end side show the Pearson's correlation values (r) with the first 34 best sensors. The 3 plots in the middle show the actual vs. the predicted signals. Scalp maps represent the correlation (decoding accuracy) for each joint.

FIGS. 19, 20 and 21 show the decoding accuracy (DA) results and the scalp map for each of the three predicted (decoded) trajectories in (x,y,z), respectively, space for right ankle, knee and hip obtained by using the best electrodes. FIG. 22 shows the decoding results and the scalp map of the predicted angular velocity for ankle, knee and hip. (See also FIG. 23).

Table 5 shows the r and SNR values for the spatial configuration and the angular velocity for the right ankle, knee and hip for illustration purposes. In real-time control mode, the predicted signals can be utilized to drive a robotic exoskeleton or to remotely control a robot in space or earth.

TABLE 5

Correlation coefficient and signal to noise ratio (dB)
for the prediction of different walking parameters.
The numbers represent mean ± standard deviation.

|  | R | SNR (dB) |
|---|---|---|
| Ankle | | |
| X | 0.52 ± 0.06 | 0.79 ± 0.65 |
| Y | 0.69 ± 0.04 | 2.24 ± 0.28 |
| Z | 0.83 ± 0.02 | 4.38 ± 1.45 |
| Ang. Vel. | 0.67 ± 0.04 | 2.24 ± 0.89 |
| Knee | | |
| X | 0.63 ± 0.09 | 1.88 ± 0.86 |
| Y | 0.54 ± 0.05 | 1.01 ± 0.37 |
| Z | 0.74 ± 0.07 | 3.10 ± 1.23 |
| Ang. Vel. | 0.80 ± 0.04 | 3.98 ± 1.24 |
| Hip | | |
| X | 0.61 ± 0.01 | 1.07 ± 1.15 |
| Y | 0.67 ± 0.03 | 1.64 ± 0.17 |
| Z | 0.61 ± 0.05 | 1.01 ± 0.56 |
| Ang. Vel. | 0.72 ± 0.02 | 2.68 ± 0.33 |

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of decoding neural activity for a brain computer interface (BCI) system, comprising the steps of:
   recording noninvasively acquired electroencephalography (EEG) signals of a subject in a time domain when the subject observes movement of a stimulus while the subject is simultaneously imagining movement of a limb tracking the movement of the stimulus;
   continuously decoding only the recorded EEG signals having a frequency of less than 4 Hz and in the time domain associated with the observed movement and the imagined movement; and
   correlating fluctuations in amplitude of the decoded recorded EEG signals with an intent of the subject.

2. The method of claim 1, comprising a further step of generating command signals for controlling movement of a device operably associated with the BCI system, wherein the command signals are associated with the intent of the subject.

3. The method of claim 2, wherein the device is a cursor displayed on a display, the cursor movable in two dimensions on the display based on EEG signals of the subject.

4. The method of claim 2, wherein the device is a prosthetic device movable in three dimensions based on EEG signals of the subject.

5. The method of claim 1, wherein the subject is imagining movement of the limb in at least two dimensions when tracking the movement of the stimulus.

6. The method of claim 5, wherein the decoded EEG signals are associated with observed or imagined hand movement in a human subject.

7. The method of claim 5, wherein the decoded EEG signals are associated with observed or imagined bipedal movement in a human subject.

8. A method of identifying a neural biomarker of a movement condition, comprising the steps of:
   recording noninvasively acquired electroencephalography (EEG) signals of a subject in a time domain when the subject observes movement of a stimulus while the subject is simultaneously imagining movement of a limb tracking the movement of the stimulus;
   continuously decoding only the recorded EEG signals having a frequency of less than 4 Hz and in the time domain associated with the observed movement and the imagined movement; and
   correlating fluctuations in amplitude of the decoded recorded EEG signals with a biomarker of a movement condition.

9. The method of claim 8, wherein the movement condition is associated with a movement disorder due to a neurological condition, a developmental disorder, or abnormal aging.

10. The method of claim 8, wherein the subject is imagining movement of the limb in at least two dimensions when tracking the movement of the stimulus.

11. The method of claim 10, wherein the decoded EEG signals are associated with observed or imagined hand movement in a human subject.

12. The method of claim 10, wherein the decoded EEG signals are associated with observed or imagined bipedal movement in a human subject.

* * * * *